US007855293B2

(12) United States Patent
Haalck et al.

(10) Patent No.: US 7,855,293 B2
(45) Date of Patent: Dec. 21, 2010

(54) 3-SPIRO-CYANIN FLUOROCHROMES AND THEIR USE IN BIOASSAYS

(76) Inventors: Lutz Haalck, Gemenweg 101, 48149 Muenster (DE); Erk Gedig, Hammer Strasse 83, Muenster (DE); Hans-Juergen Hoelpert, An der Werseaue 18, 48157 Muenster (DE); Viola Podsadlowski, Stiftsherrenstrasse 16, 48143 Muenster (DE)

( * ) Notice: Subject to any disclaimer, the term of this patent is extended or adjusted under 35 U.S.C. 154(b) by 822 days.

(21) Appl. No.: 10/130,547

(22) PCT Filed: Sep. 3, 2001

(86) PCT No.: PCT/EP01/10130

§ 371 (c)(1),
(2), (4) Date: Sep. 19, 2002

(87) PCT Pub. No.: WO02/26890

PCT Pub. Date: Apr. 4, 2002

(65) Prior Publication Data
US 2003/0138791 A1 Jul. 24, 2003

(30) Foreign Application Priority Data
Sep. 19, 2000 (DE) ............................. 100 46 215

(51) Int. Cl.
C07D 401/04 (2006.01)
C07D 209/54 (2006.01)
(52) U.S. Cl. ......................... 546/17; 548/408
(58) Field of Classification Search .................. 546/17; 514/315, 278; 548/408
See application file for complete search history.

(56) References Cited

U.S. PATENT DOCUMENTS

| 4,981,977 | A | | 1/1991 | Southwick et al. ........... 548/455 |
| 5,268,486 | A | * | 12/1993 | Waggoner et al. ........... 548/427 |
| 5,486,616 | A | | 1/1996 | Waggoner et al. ........... 435/217 |
| 5,534,416 | A | | 7/1996 | Millard et al. |
| 5,556,959 | A | | 9/1996 | Brush et al. .............. 536/25.32 |
| 5,569,587 | A | | 10/1996 | Waggoner et al. .............. 435/6 |
| 5,582,977 | A | | 12/1996 | Yue et al. ........................ 435/6 |
| 5,597,696 | A | | 1/1997 | Linn et al. ....................... 435/6 |
| 5,627,027 | A | | 5/1997 | Waggoner et al. ............... 435/6 |
| 5,986,086 | A | | 11/1999 | Brush et al. ............... 536/26.26 |
| 6,004,536 | A | | 12/1999 | Leung et al. .................. 424/9.6 |
| 6,027,709 | A | | 2/2000 | Little et al. .................. 424/1.65 |
| 6,048,982 | A | | 4/2000 | Waggoner et al. ............. 548/148 |
| 6,083,485 | A | | 7/2000 | Licha et al. ................... 424/9.6 |
| 6,114,350 | A | | 9/2000 | Randall et al. ................ 514/311 |
| 6,197,956 | B1 | | 3/2001 | Randall et al. ................. 544/51 |
| 6,204,389 | B1 | | 3/2001 | Randall et al. ................ 548/152 |
| 6,224,644 | B1 | | 5/2001 | Randall et al. ................ 548/152 |
| 6,319,488 | B1 | | 11/2001 | Licha et al. ................... 424/9.6 |
| 6,329,531 | B1 | | 12/2001 | Turner et al. ................. 548/455 |
| 6,534,041 | B1 | | 3/2003 | Licha et al. ................... 424/9.6 |
| 6,740,755 | B2 | | 5/2004 | Caputo et al. ................. 544/310 |
| 6,974,698 | B1 | * | 12/2005 | Miller et al. .................. 435/375 |
| 2002/0077487 | A1 | | 6/2002 | Leung et al. ................. 548/414 |
| 2003/0170179 | A1 | | 9/2003 | Licha et al. ................... 424/9.6 |

FOREIGN PATENT DOCUMENTS

| DE | 3912046 | A1 | | 3/1990 |
| DE | 19940394 | A1 | | 3/2001 |
| EP | 0710668 | A2 | | 5/1996 |
| EP | 0710668 | A3 | | 3/1997 |
| JP | 07114140 | | * | 5/1995 |
| JP | 07271065 | | * | 10/1995 |
| JP | 08292590 | | * | 12/1996 |
| JP | 09290570 | | * | 11/1997 |
| JP | 10-195319 | | | 7/1998 |
| JP | 10-219124 | | | 8/1998 |
| WO | WO 90/03383 | | * | 4/1990 |
| WO | WO 93/06482 | | | 4/1993 |
| WO | WO 98/30992 | A2 | | 7/1998 |
| WO | WO 98/30992 | A3 | | 7/1998 |
| WO | 98/47538 | A2 | | 10/1998 |
| WO | WO 98/58942 | A | | 12/1998 |

OTHER PUBLICATIONS

Caplus English Abstract JP 09090562, Sumioka Koichi et al, 1997.*
Caplus English Abstract JP 08292589, Matsuayashi Tatsuro et al—1996.*
Caplus English Abstract JP 08152729, Maruyama Atsushi et al, 1996.*
Mujumdar et al: "Cyanine Dye Labeling Reagents: Sulfoindocyanine Succinimidyl Esters",Bioconjugate Chemistry, vol. 4, No. 2, Mar. 3, 1993.
Randolph J. B. et al: "Stability, Specificity and Fluorescence Brightness of Multiply-Labeled . . . Probes", Nucleic Acids Research,vol. 25, #14, Jul. 15, 1997.
Patent Abstracts of Japan, vol. 1998, No. 12, Oct. 31, 1998 & JP10-195319, Mitsubishi Paper Mills Ltd.
Rodriguez et al: Synthesis of 2'-Alkylspiro[2-X-cyclohexan-1,3'-3'H-indole](X=H; X=CH$_3$) . . . Compound, vol. 63, No. 13, 1998.

(Continued)

Primary Examiner—Rita J Desai
(74) Attorney, Agent, or Firm—Bacon & Thomas, PLLC

(57) ABSTRACT

The invention concerns sterically shielded, stabilized fluorescent dyes based on symmetrical or unsymmetrical 3-spiro-cyanines and their utilization as marker-molecules in analytical procedures. The fluorescent dyes according to the invention are characterized by a strongly reduced proneness towards aggregation due to the insertion of bulky spiro-substituents and thus enable to reach a high degree of coupling to the target molecule without a significant loss of fluorescence due to self quenching effects. They therefor exhibit a high quantum yield and are thus excellently suitable as fluorescent dyes, especially as NIR-fluorescent dyes, for the coupling or binding to biological and non-biological target molecules used in analytical methods. The analytical methods comprise all methods in which fluorescence-optical methods are used to detect biological and non-biological molecules.

13 Claims, 13 Drawing Sheets

OTHER PUBLICATIONS

Figure 1:
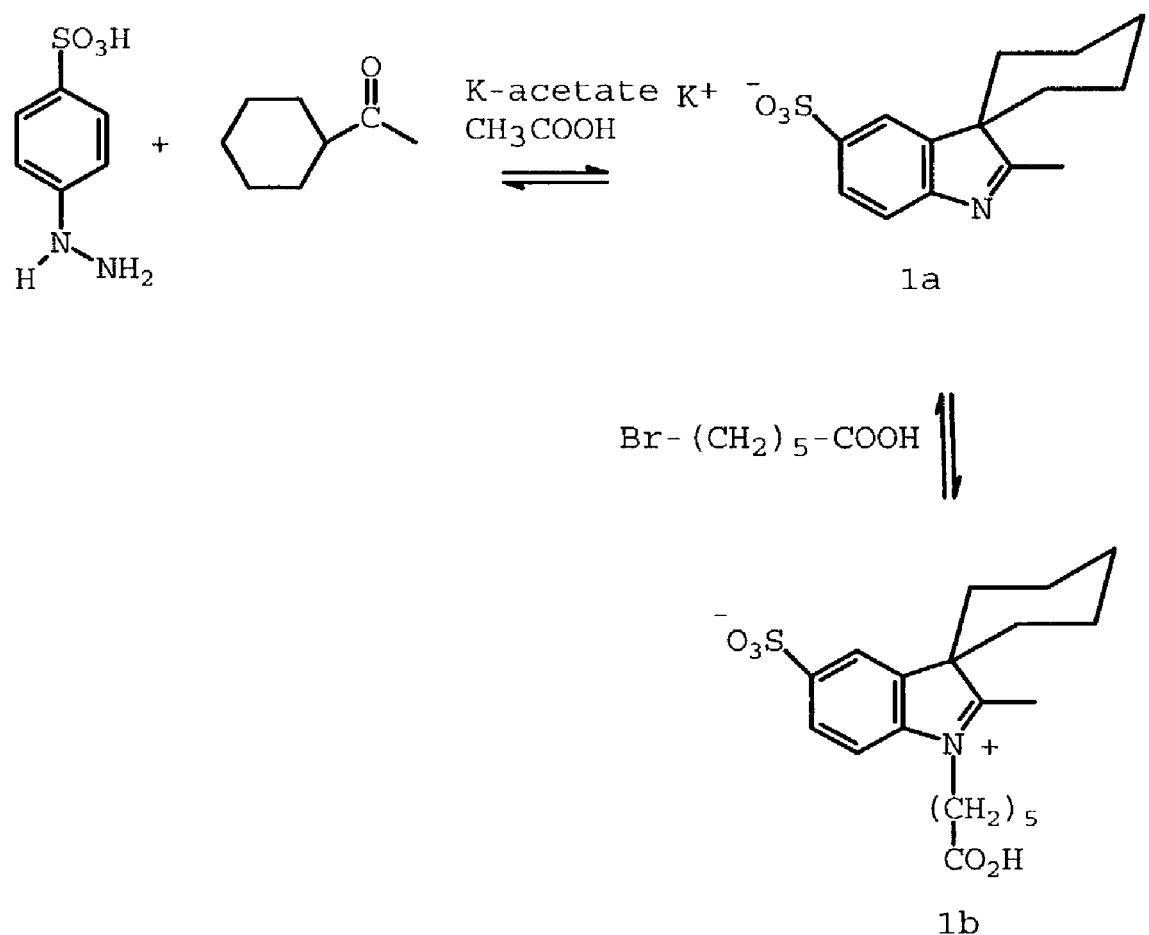

John B. Randolph and Alan S. Waggoner, "Stability, specificity and fluorescence brightness of multiply-labeled fluorescent DNA probes", Nucleic Acids Research, 1997, vol. 25, No. 14, pp. 2923-2929.

Ratnakar B. Mujumdar et al., "Cyanine Dye Labeling Reagents: Sulfoindocyanine Succinimidyl Esters", Bioconjugate Chemistry, Mar./Apr. 1993, vol. 4, No. 2, 1993, pp. 105-111.

* cited by examiner

3-SPIRO-CYANIN FLUOROCHROMES AND THEIR USE IN BIOASSAYS

The invention concerns sterically shielded, stabilized fluorescent dyes on the basis of symmetrical or unsymmetrical 3-spirocyanines and their application as marker-molecules in analytical methods.

Fluorescent dyes are increasingly used to label enzymes, antibodies and nucleic acids and employed in immunoassays, fluorescence microscopy and for sequencing. Traditionally, fluorescent dyes are used which are excited using light from the UV or visible region of the electromagnetic spectrum. Their excitation and emission spectra overlap with the given natural serum fluorescence, making them only partially suitable for analysis of natural samples (e.g. blood and serum samples, cells). Fluorescent dyes with excitation wavelength in the near infrared region of the light spectrum are thus used since a couple of years, allowing the measurement of biological samples with low background fluorescence and concomitantly increased sensitivity.

The demand of biochips (protein-, DNA-arrays) that enable the specific detection of proteins as well as DNA or fragments thereof, grows exponentially due to scientific developments in the proteomics and genomics sector. Most of these applications also involve the use of fluorescent dyes.

The use of reactive and water soluble NIR-fluorophores for coupling with biomolecules was first described in U.S. Pat. No. 5,268,486. Chemical groups are inserted, preferably as N-substituents, that are suitable for coupling with reactive amino acid side chains (e.g. amino-, thio-, carbonyl-, or hydroxy groups), some of these chemical groups being isothiocyanates, thiocyanates, hydrazines, hydroxy-succinimidylesters, disulfides etc. This principle was extended in recent time beyond symmetrical cyanomethine dyes (2,2'-indo-cyanines) to encompass structurally related merocyanines and styrylcyanine dyes.

All dyes of the cyanine type as well as other commonly used fluorescent dyes, e.g., rhodamines, show a characteristic behavior in aqueous solution. Due to the planar chemical structure (arrangement) of the fluorophores, aggregation or dimer-formation occurs especially at higher coupling ratios (molar ratio dye/protein; D/P>5). This leads to drastically reduced fluorescence due to radiation free intermolecular transition processes. This phenomenon arises in solutions, e.g. in presence of high concentrations of salts, as well as with protein bound fluorophores. Dyes without additional hydrophilic groups and amino-substituted cyanine dyes are especially sensitive to this problem.

The dyes described in U.S. Pat. No. 5,268,486 and DE 39 120 46 could only reduce but not eliminate this problem through insertion of arylsulfonates to raise their water solubility. In general, the quantum yield in aqueous solutions, however, is reduced significantly compared to organic solvents.

Many different interactions are utilized for the labelling of oligonucleotides or DNA/RNA. Besides the classical intercalation dyes like ethidium bromide, the specific ionic binding to phosphate groups of nucleotides (U.S. Pat. No. 5,410,030) by positively charged dyes and various covalent couplings of dyes to modified purin/pyrimidinbases (U.S. Pat. No. 6,027,709) as well as to phosphate groups of nucleotides are feasible. This development reflects the high increase in demand of fluorescent dyes for DNA labelling and sequencing.

It is the task of the presented invention to suggest fluorescent dyes that exhibit a high quantum yield and simultaneously a low tendency towards aggregation. Furthermore, these fluorophores shall cover a wide variety of different ways to bind to a vast number of target molecules and thus allow for a wide variety of application fields.

The task is solved by the characteristic features described in claim 1. The other dependant claims show further advantageous refinements (embodiments).

The application of fluorophores according to the invention is described by claims 1 to 13. Fluorescent dyes are suggested according to this invention, which are based on a basic structure of symmetrical or unsymmetrical cyanine dyes with at least one sterically demanding spiro-substituent in 3-position of the indole headgroup. These fluorescent dyes will be referred to as spironines. The fluorescent dyes according to the invention have the following basic structure:

Fluorescent dye of the general formula A-Z-A' with

A a group of general formula I

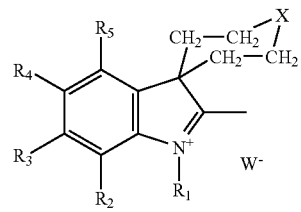

wherein X is

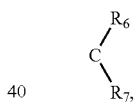

O, S, SO, $SO_2$ or

$W^-$=any counter ion, preferably halogenide, perchlorate or tosylate.

A' is selected from a group having the general formulas II to V,

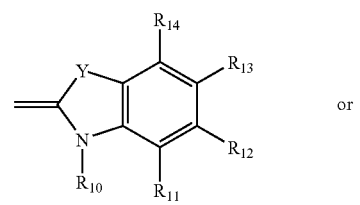

-continued

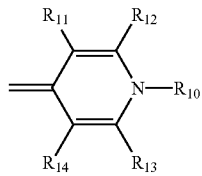

or

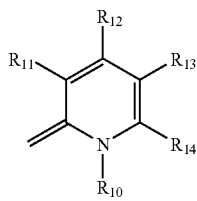

or

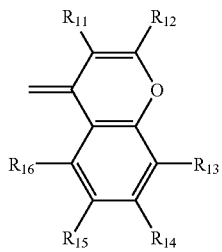

wherein Y is O, S, NR$_{17}$,

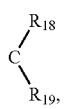 or 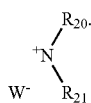

and T is

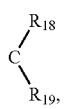,

O, S, SO, SO$_2$ or

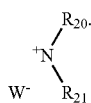

Z represents a group with the general formula VI or VII

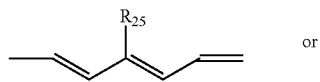 or

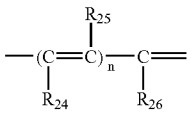

with n' is an integer selected from the group consisting of 0, 1, 2, or 3 or wherein at least one of the residues R$_1$ to R$_{26}$ is selected from a group consisting of a) a chemical reactive group for covalent coupling to a target molecule or b) an ionic group for coupling to a target molecule by ionic interaction forces or c) a lipophilic group for coupling to a target molecule by adsorption.

By means of the selective introduction of the groups a) to c) into the fluorescent dye, it is made possible to bind the dye to different target molecules and thus allow for different fields of applications.

The other groups are chosen independently from each other from the groups H, alkyl (C$_1$-C$_{10}$), alkoxy (C$_1$-C$_{10}$), trifluoromethyl, halogen, sulfonic acid, sulfonate, phosphoric acid and phosphonate.

Through use of cyanine dyes with bulky substituents in 3-position of the indole headgroup, especially cyclic substituents, so called spirones, e.g. spiro-1'-cyclohexan, spiro-4'-1'-piperidine, 4'-1'-tetrahydropyrane, spiro-4'-1'-tetrahydrothipyrane, spiro-4'-1'-oxotetrahydro-thiopyrane, spiro-4'-1',1'-dioxotetrahydrothiopyrane, the central polymethine chain is shielded extensively.

Surprisingly, it could be shown according to the invention that fluorescent dyes substituted like this exhibit a significant reduced tendency towards aggregation. Furthermore, a higher photostability compared to commercially available cyanine dyes was observed. Particularly interesting in this matter is the utilization of cyclic substituents, e.g. substituted spiro-cyclohexanes, spiro-piperidines, spiro-tetrahydrooxopyranes or spiro-tetrahydrothiopyranes. Based on these spiro compounds, a new elegant route is created to control the water solubility by choosing a polar or non-polar substituent as well as to positively influence the binding behavior of the dye by insertion of reactive groups R$_x$ or ionic groups. The shielding and thus stabilizing effect of the spiro groups can be amplified through further insertion of bulky substituents at the spiro-residues.

The invention based fluorophores can be excited by light of a wavelength of 600-1000 nm. Typical for the fluorescent dyes are high molar extinction coefficients and very high quantum yields. The stokes shift normally is at least 15 nm. A utilization of these dyes in a broad field of applications is made possible by cost effective laser diodes emitting light in the range of 670-830 nm.

The groups R$_1$, R$_4$, R$_6$ to R$_{10}$, R$_{13}$ and R$_{17}$ to R$_{21}$ in the general formulas I to V are of higher significance. These positions are especially suitable for insertion of substituents to increase the water solubility, the insertion of non-polar substituents to increase the lipophily and/or at least one reactive group R$_x$ for the coupling to biomolecules.

Thus, the fluorescent dyes contain at least one reactive group R$_x$ for the coupling to target molecules in the general formulas I to VII advantageously as groups R$_1$, R$_4$, R$_6$ to R$_{10}$, $R_{13}$ and $R_{17}$ to $R_{21}$, particular advantageously s groups $R_1$, $R_6$ to $R_{10}$ and $R_{18}$ to $R_{21}$ and particular advantageously as groups $R_6$ to $R_9$ and $R_{18}$ to $R_{21}$.

The reactive group $R_x$ can be covalently bound directly to the dye or through a bridge made by several atoms and exhibits a suitable chemistry.

The reactive group $R_x$ is preferentially chosen from the group of carboxylic acids, activated esters, acylazides, acylhalogenides, acylnitriles, aldehydes, anhydrides, arylamides, alkyl halides, anilines, alkylsulfonates, arylhalogenides, thioles, azides, aziridines, borates, carbodiimides, diazoalkanes, epoxides, glyceroles, haloacetamines, halotriazines, hydrazines, hydroxylamines, imidoesters, isocyanates, isothiocyanates, maleimides, phosphoramidites, silyl halides, sulfonates and sulfonylchlorides. Subsequently some exemplary groups $R_x$ and their structures are shown.

activated carboxylic acid

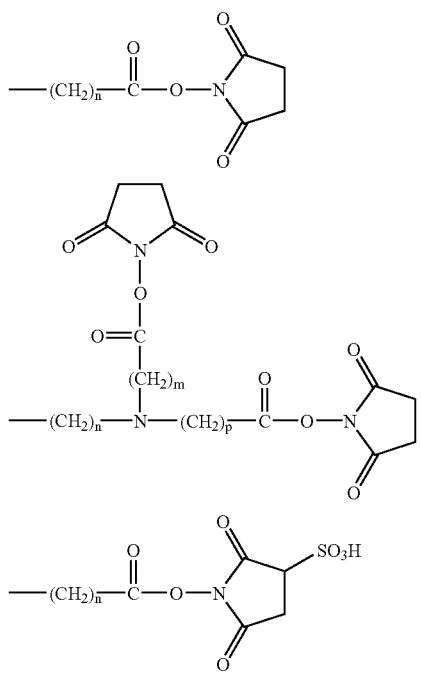

with n, m and p independently from each other equal to 1 to 8 carbodiimides

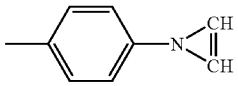

with n=1 to 8 anhydrides

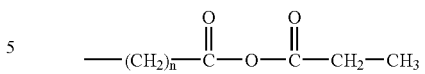

with n=1 to 8 carboxylic acid azides

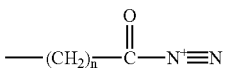

With n=1 to 8

Coupling of nucleophiles through epoxides

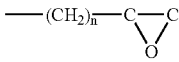

with n=1 to 8 isothiocyanates

—(CH$_2$)$_n$—NCS

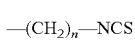

with n=1 to 8 isocyanates

—(CH$_2$)$_n$—NCO

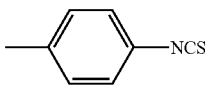

with n=1 to 8 aziridines

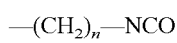

with n=1 to 8

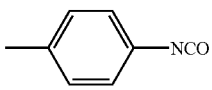

maleimides

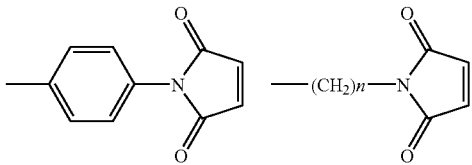

with n=1 to 8 pyridyl-disulfide activated groups

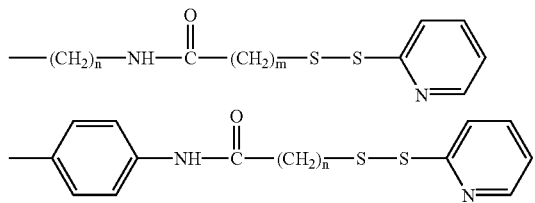

with n and m independently from each other equal to 1 to 8 halodi- and triazines

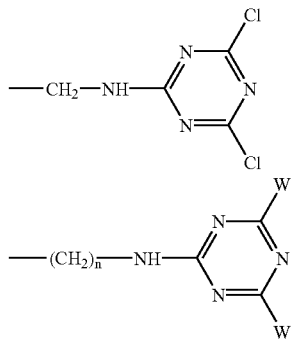

with W=chlorine or bromine and n=1 to 8 vinylsulfones

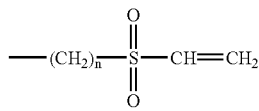

with n=1 to 8 acylimidazoles

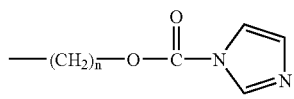

with n=1 to 8 phosphoramidite

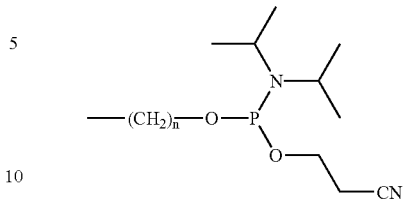

with n=1 to 8

Tab. 1 shows an overview over possible ways of creating dye-conjugates by covalent binding.

Additionally, the fluorescent dye according to the invention may contain at least one ionic group. Some of the preferred ionic groups for example are selected from the group of carboxylic acids, sulfonic acids, sulfonates, phosphoric acids, phosphonates, phosphordiesters, phosphortriesters and primary to quaternary amines. Advantageously at least one of the groups $R_1$, $R_4$, $R_6$ to $R_{10}$, $R_{13}$ and $R_{17}$ to $R_{21}$, particular advantageously at least one of the groups $R_1$, $R_6$ to $R_{10}$ and $R_{18}$ to $R_{21}$ and advantageously at least one of the groups $R_6$ to $R_9$ and $R_{18}$ to $R_{21}$.

Further, one group of the group A, chosen from the group $R_1$, $R_6$ to $R_9$, and one group of the group A', chosen from the group $R_{10}$, $R_{17}$ to $R_{21}$, can represent ionic groups with opposite charges. This has the special advantage that an additional stabilization of the fluorescent dye is made possible by this intramolecular ionic bridge. It is also possible for the ionic groups in the groups A and A' to have the same charge and to form a complex with an ion of opposite charge. It is preferred hereby to have two anionic groups that form a complex with a metal-ion from the 1. to 3. main- or subgroup.

To raise the solubility in water, for example groups like carbon acids, carbohydrates, sulfonic acids, sulfonates, phosphates, phosphonates, amines, halogens, polyoles or polyethers could be chosen and inserted at any position of the fluorescent dye, advantageously as at least one of the groups $R_1$, $R_4$, $R_6$ to $R_{10}$, $R_{13}$ and $R_{17}$ to $R_{21}$, particular advantageously as at least one of the groups $R_1$, $R_6$ to $R_{10}$ and $R_{18}$ to $R_{21}$ and most particular advantageously as at least one of the groups $R_6$ to $R_9$ and $R_{18}$ to $R_{21}$.

To raise the lipophily, long-chain saturated or unsaturated alkyl groups (preferably $C_6$ to $C_{18}$) or fatty acids/fatty alcohols could be chosen and inserted at any position of the fluorophor, advantageously at least one of the groups $R_1$, $R_4$, $R_6$ to $R_{10}$, $R_{13}$ and $R_{17}$ to $R_{21}$, particularly advantageous at least one of the groups $R_1$, $R_6$ to $R_{10}$ and $R_{18}$ to $R_{21}$ and especially advantageous at least one of the groups $R_6$ to $R_9$ and $R_{18}$ to $R_{21}$.

In another advantageous embodiment of the invention two ortho residues at the aromatic ring may be combined to form at least one additional aromatic, carbo- or heterocyclic ring.

The dye can form complexes or conjugates with a biological or non-biological target molecule by creation of one or more covalent bonds using one or more groups $R_x$, the target molecule preferably being from the group of antibodies, proteins, peptides, enzyme substrates, hormones, lymphokines, lipids, phospholipids, metabolites, receptors, antigenes, haptenes, lectines, toxines, carbon hydrates, oligosaccharides, polysaccharides, nucleic acids, desoxyribonucleic acids, derivatizid desoxyribonucleic acid, derivatized nucleic acids, DNA-fragments, RNA-fragments, drugs, virus particles, virus components, yeast, yeast components, bacteria, bacteria components, blood cells, blood cell components, biologic cells, non-cellular blood components, poisons, polymers, polymer particles, glass particles, glass surfaces, plastic surfaces, plastic particles, polymer membranes, metals, conductors or semiconductors.

In another advantageous refinement fluorescent dyes are bound to the surface of or incorporated into nano- or microparticles, mostly on the basis of polymer materials. These particles can then be used advantageously in analytical methods.

The fluorescent dyes according to the invention especially distinguish themselves from the state of the art by a strongly reduced proneness towards aggregation due to the insertion of bulky spiro-substituents and thus a high degree of coupling to the target molecule without self-quenching of the fluorescence. They therefor exhibit a high quantum yield and are thus excellently suitable as fluorescent dyes, especially as NIR-fluorescent dyes, for the coupling or binding to biomolecules used in bioassays. The analytical methods comprise all methods in which fluorescence-optical methods are used to detect biomolecules. A preferred way of realization are fluorescence-immuno-tests which are based on known biochemical assays of general receptor-ligand systems, for example antibody-antigen, lectin-carbohydrate, DNA or RNA-complimentary nucleic acids, DNA or RNA-proteins, hormone receptors, enzyme-enzym co-factors, protein G or protein A-immunglobulin or avidin-biotin.

If the fluorescent dye according to the invention contains adequate nucleophilic groups, preferably amino-, thio-, or hydroxy-groups, a coupling of the dye, for example after activation as phosphoramidite, to a nucleotide becomes possible. This process is especially important for the preparation of dye-labelled (desoxy-)nucleotides, which for example can be used in sequencing machines.

Some representative fluorescent dyes according to the invention are summarized in the following.

Formula VIII with $M^+$=metal cation and with X, T, and n' as previously defined.

Formula IX

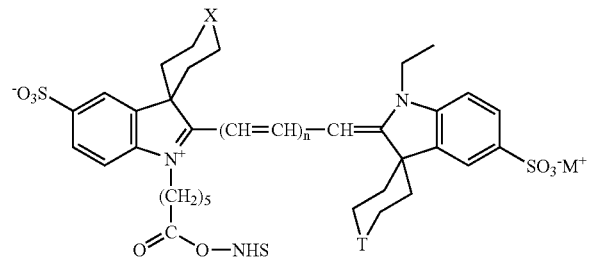

with $M+$=metal cation, NHS=N-Hydroxy-succinimide and with X, T, $W^-$ and n' as previously defined.

Formula X with X, T, $W^-$ and n' as previously defined, m is equal to 0, 1-17.

Formula XI with $M^+$=metal cation, X, Y, T, $W^-$, m and n' as previously defined.

Formula XII with X, Y, T, $W^-$, m and n' as previously defined, p is equal to 1 to 8.

Formula XIII

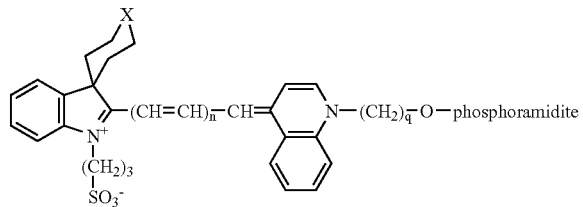

with X and n' as previously defined, q is equal to 1 to 8.

Formula XIV

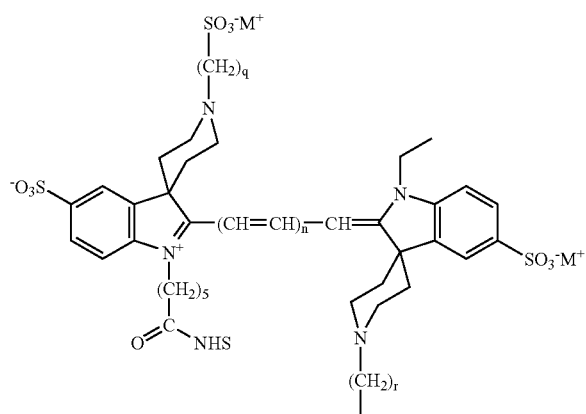

with M⁺=metal cation and n' as previously defined, NHS=N-hydroxy-succinimid, r and q independently from each other equal to 1 to 8.

Formula XV

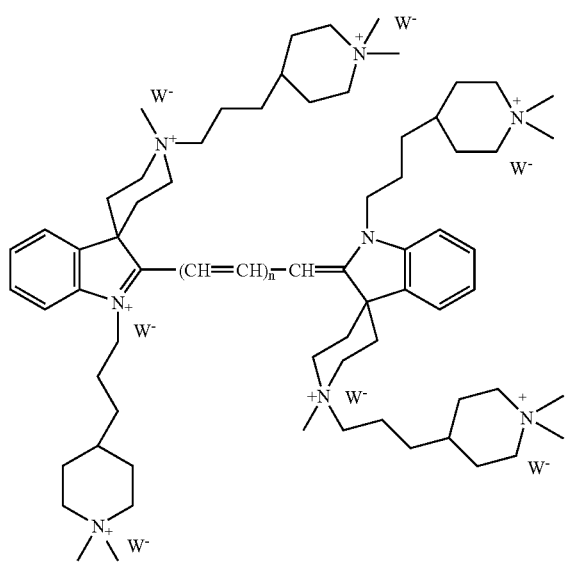

with W⁻ and n' as previously defined.

Formula XVI

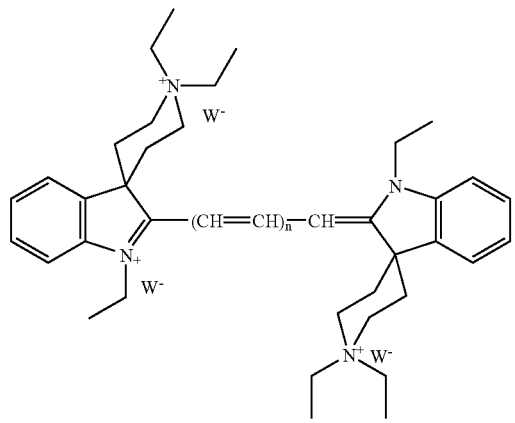

with W⁻ and n' as previously defined.

Formula XVII

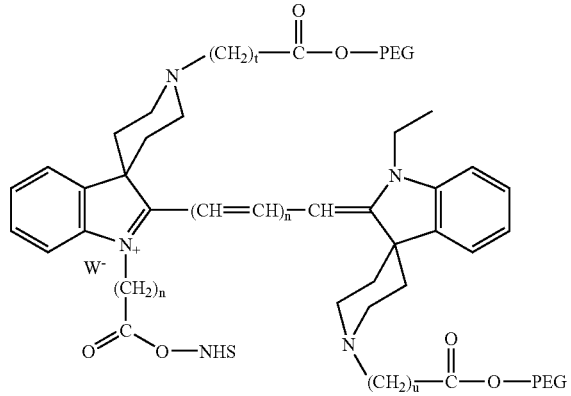

with W⁻ and n and n' as previously defined, NHS=N-hydroxy-succinimide, PEG=poly ethylen glycole and with t and u independently from each other equal to 1 to 8.

Formula XVIII

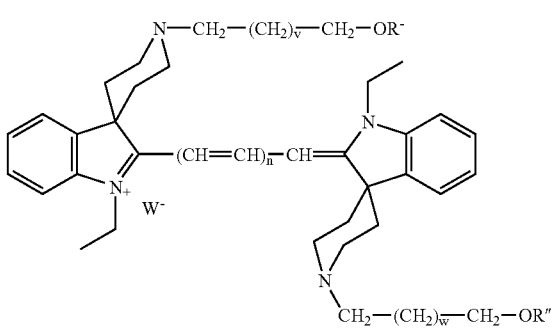

with W⁻ and n' as previously defined, R'=trityl, R''=phosphoramidite, v and w independently equal to 0 to 6.

Formula XIX

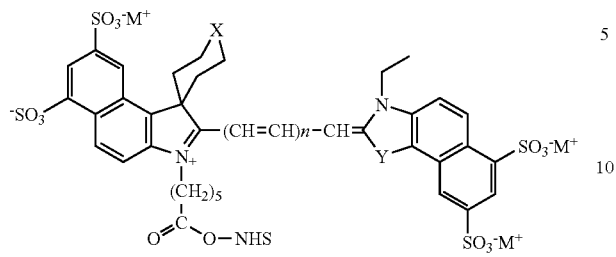

with M⁺=metal cation, X, Y, T, W⁻ and n' as previously defined.

Formula XX

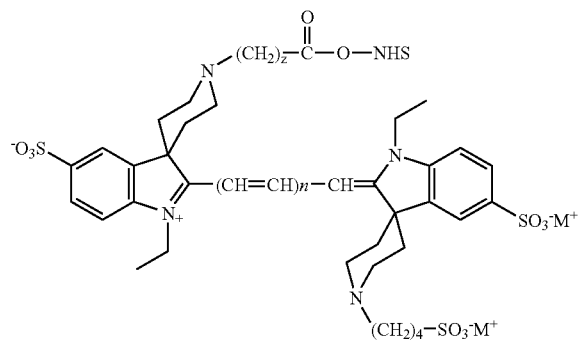

with M⁺=metal cation, X, Y, T, W⁻ and n' as previously defined, z equal to 0, 1 to 6.

The invention will be described in more detail by way of figures and examples below, without restricting it to them.

FIG. 1 Synthesis of compounds S1 to S3. (Part 1)

Figure 2:
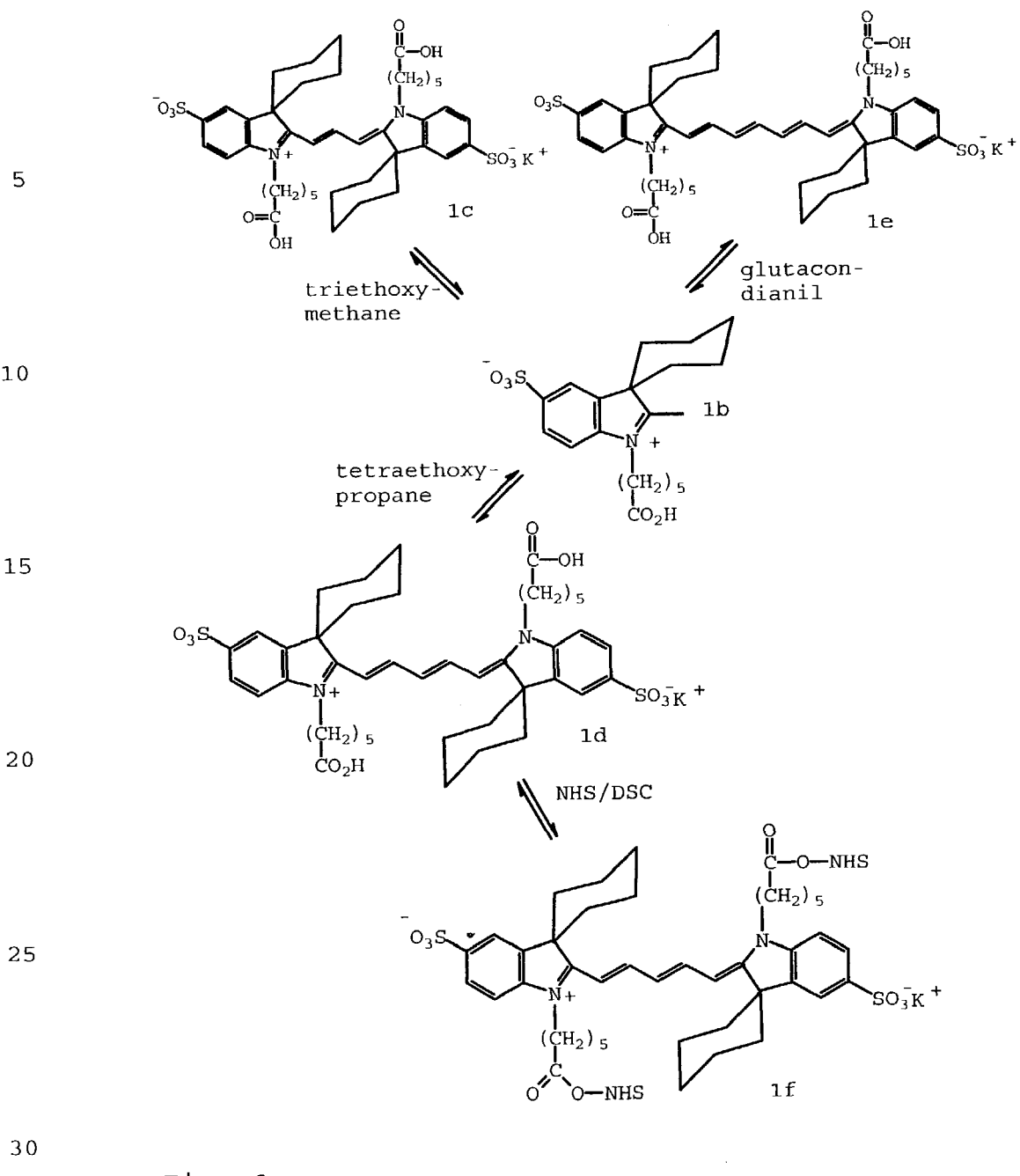

FIG. 2 Synthesis of compounds S1 to S3. (Part 2)

Figure 3:
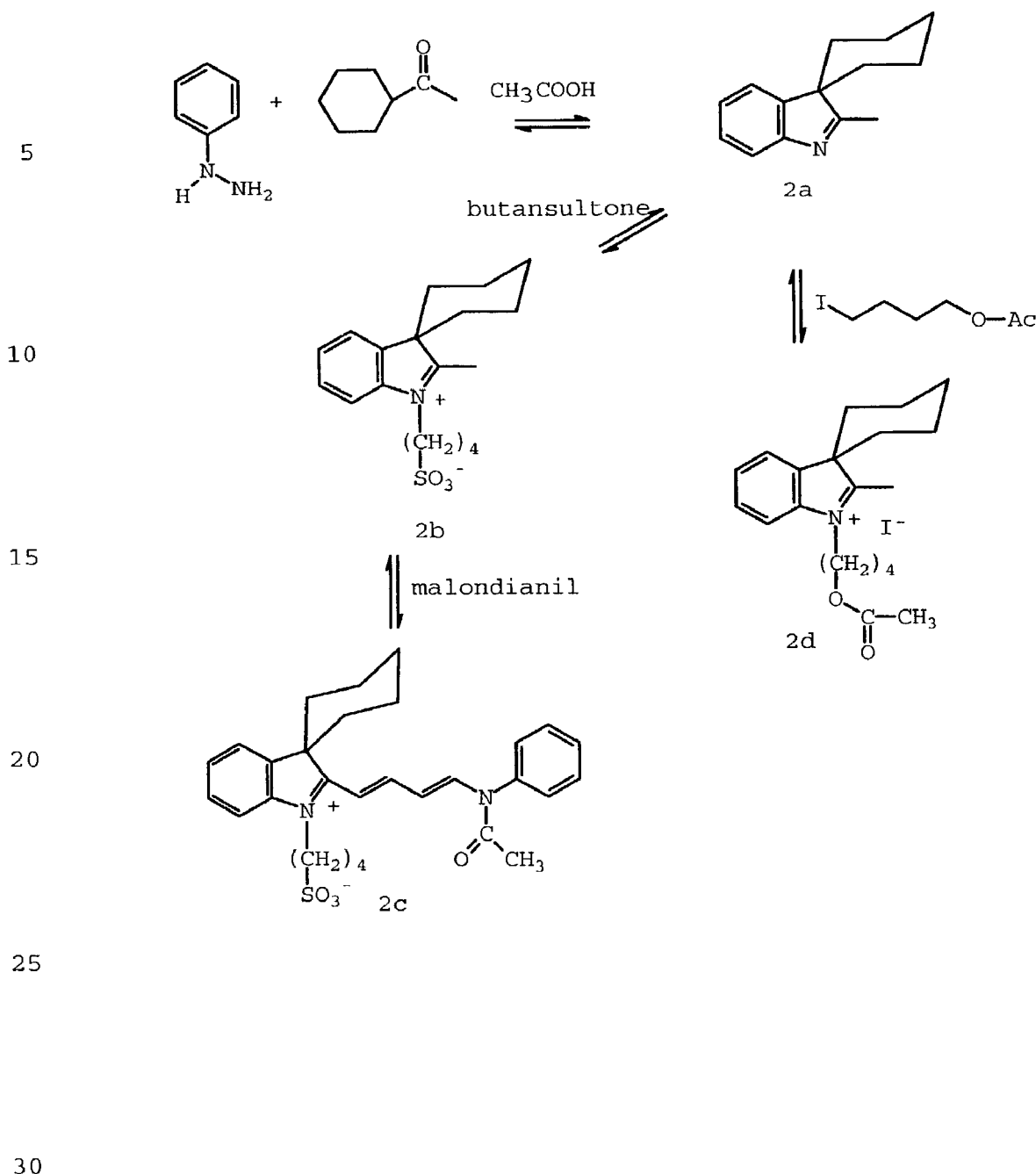

FIG. 3 Synthesis of compounds S4 to S7. (Part 1)

Figure 4:
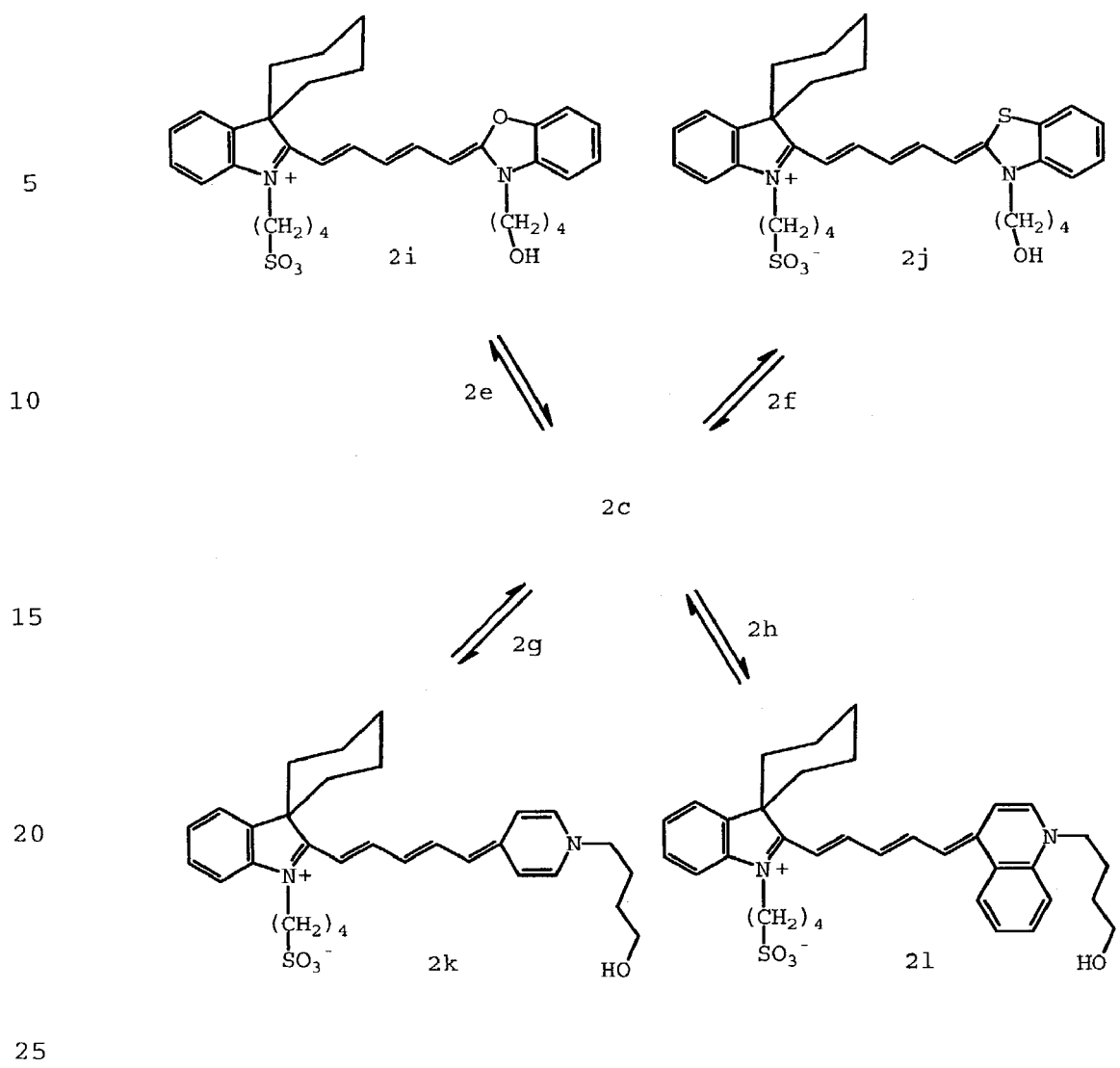

FIG. 4 Synthesis of compounds S4 to S7. (Part 2)

Figure 5:
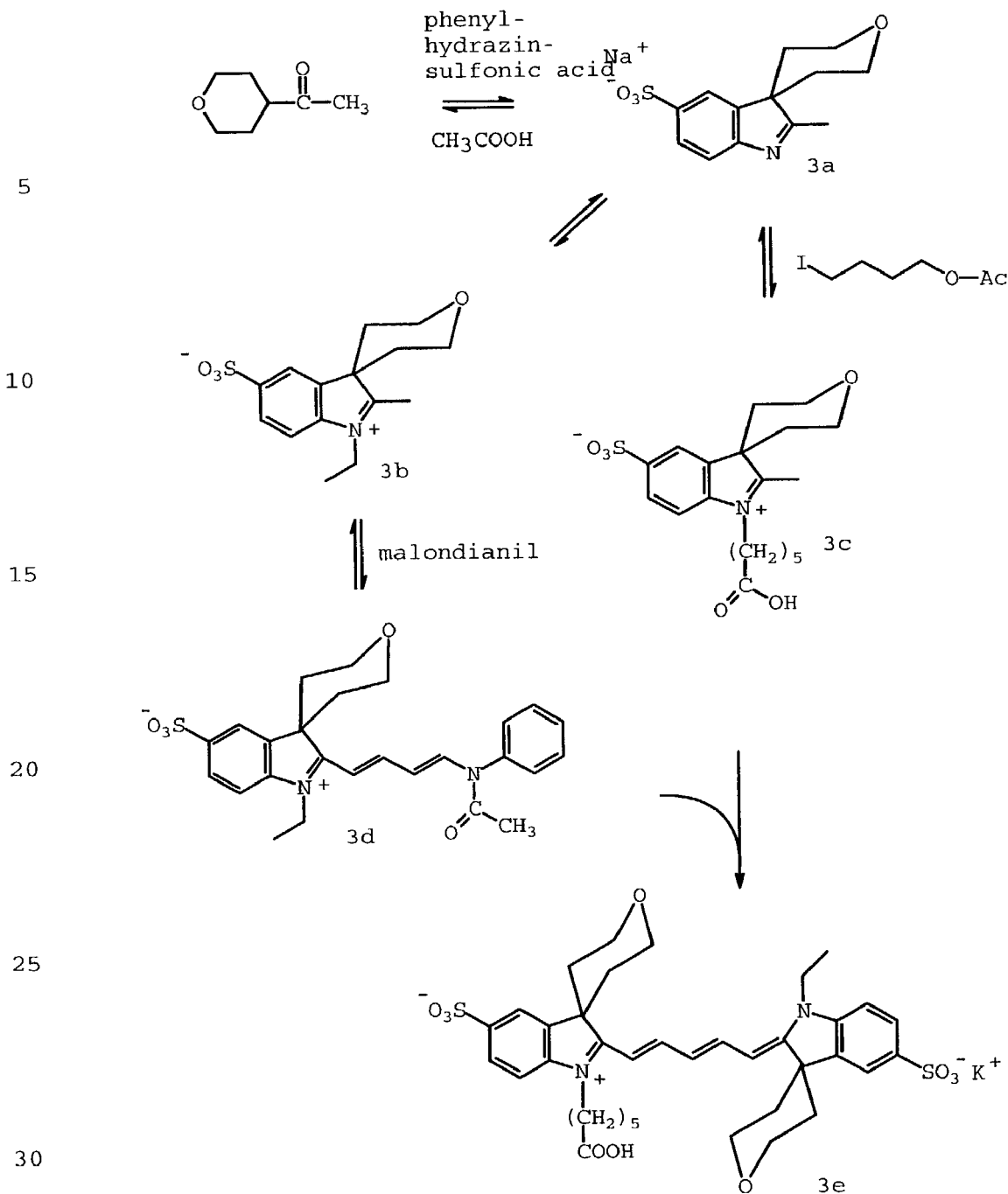

FIG. 5 Synthesis of compound S8.

Figure 6:
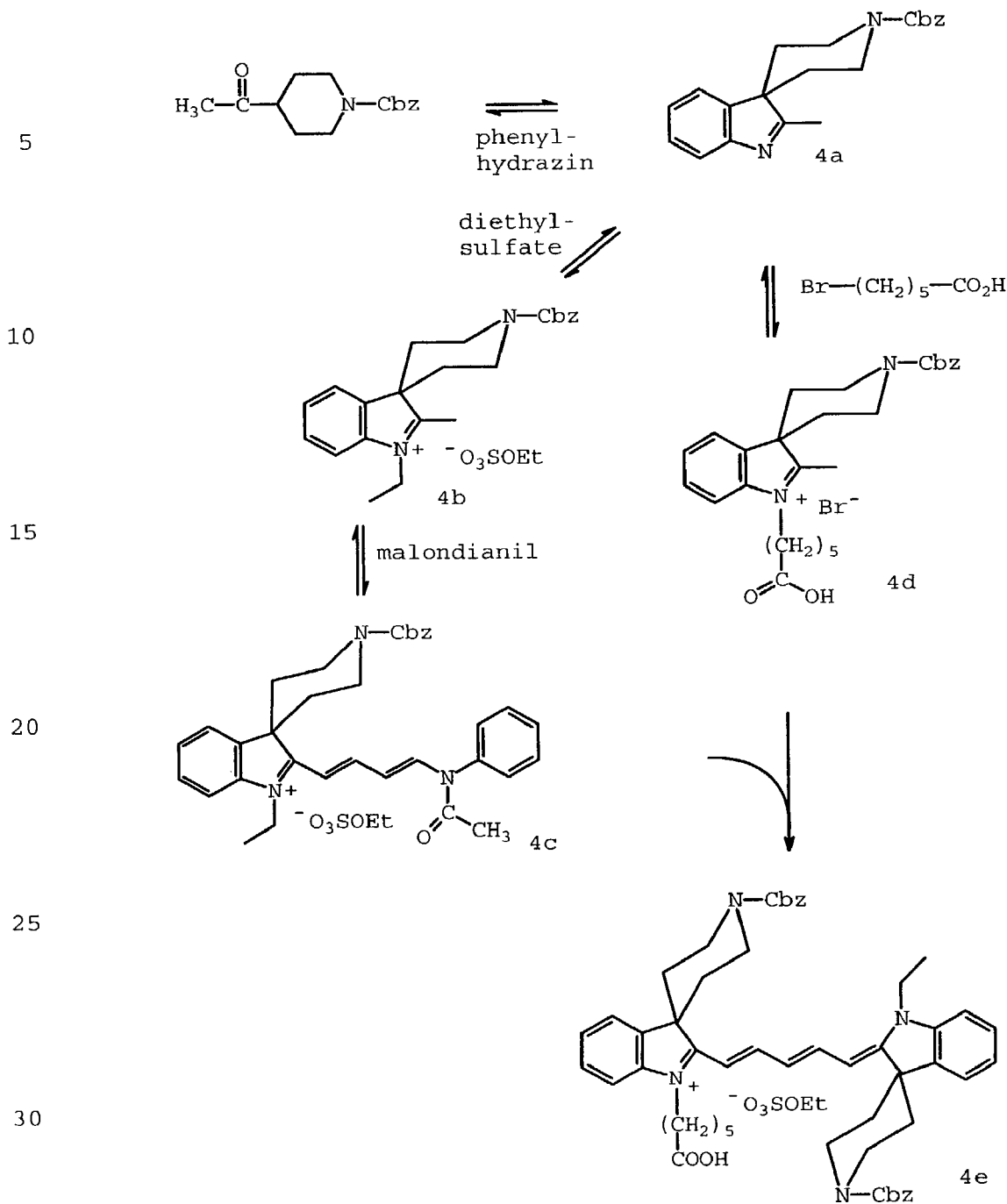

FIG. 6 Synthesis of compound S9. (Part 1)

Figure 7:
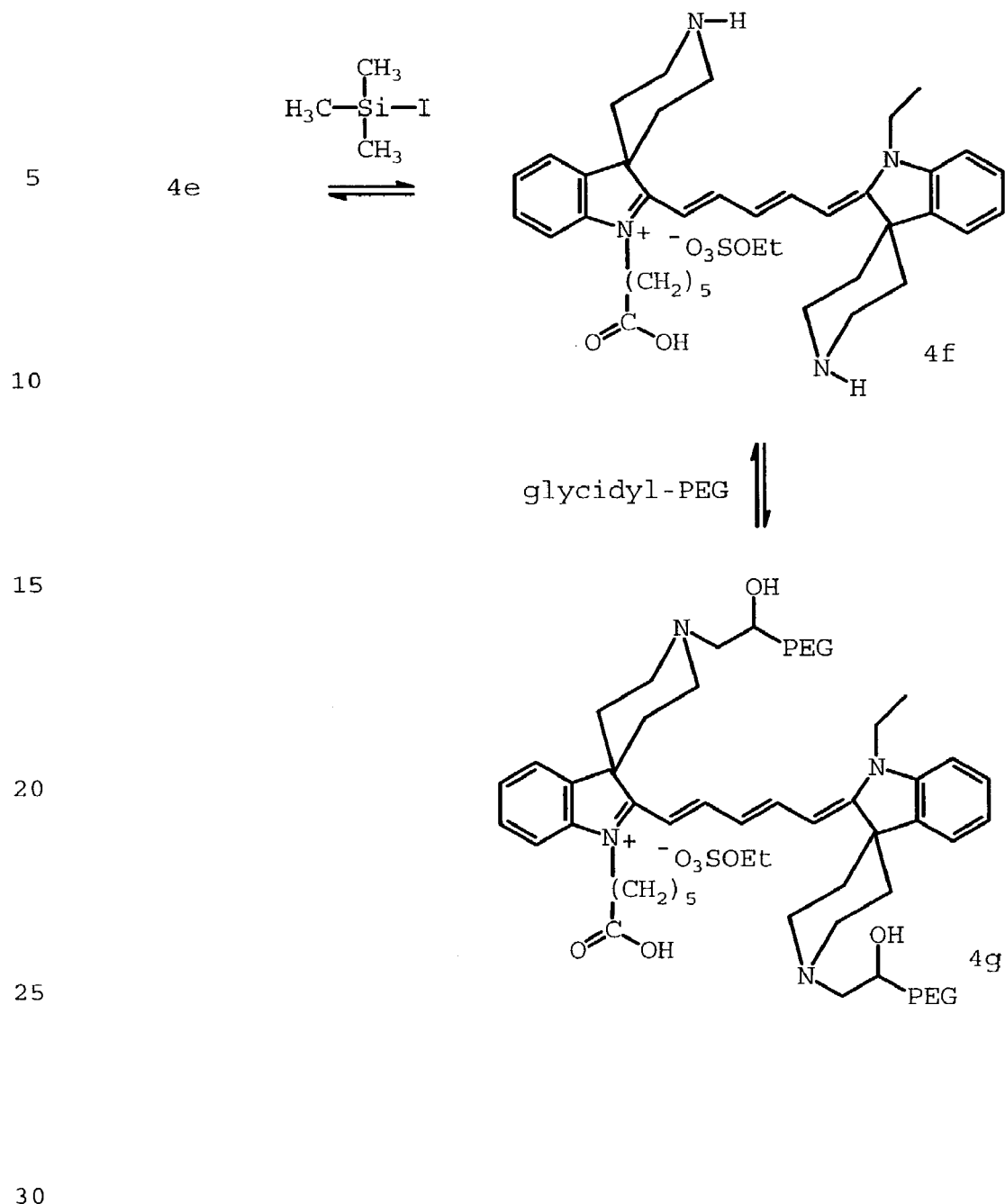

FIG. 7 Synthesis of compound S9. (Part 2)

Figure 8:
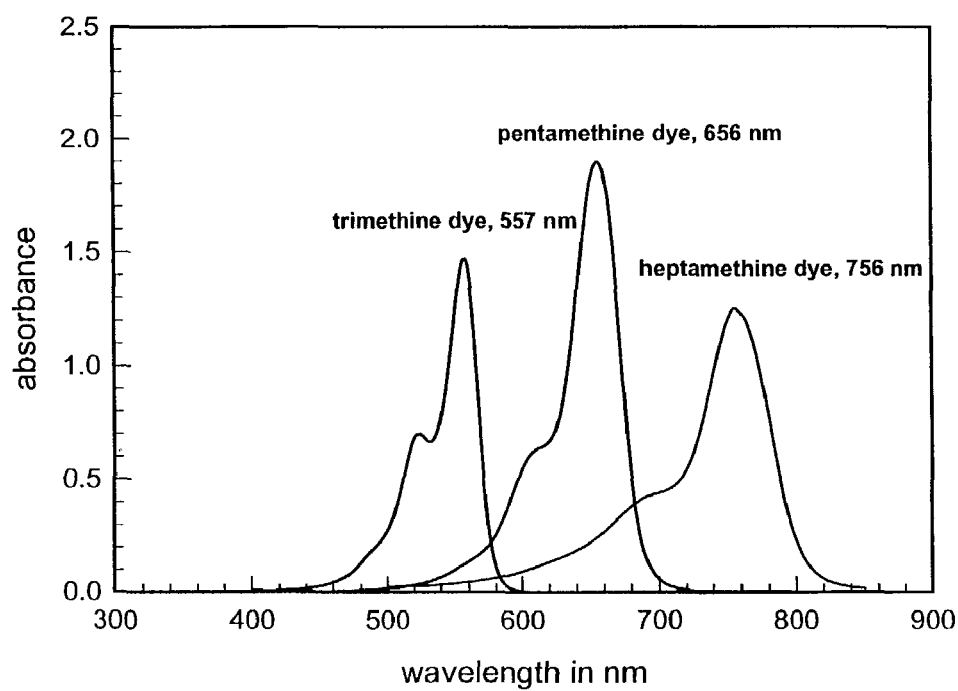

FIG. 8 Absorption spectrum of the fluorescent dyes (compounds S1 to S3) according to the invention.

Figure 9:
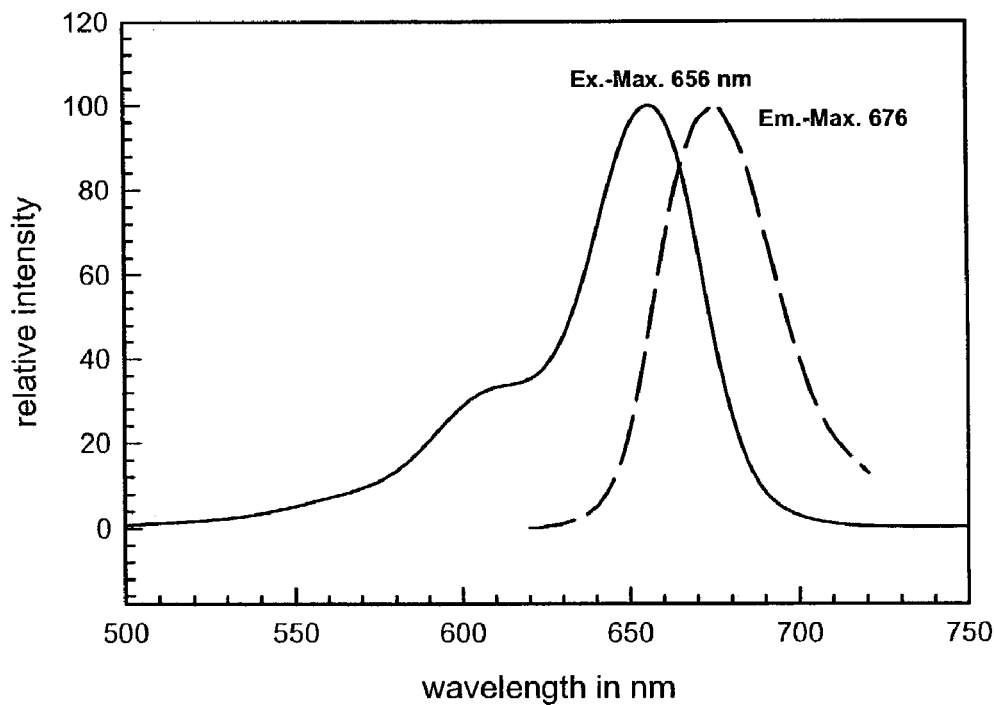

FIG. 9 Absorption- and emission-spectrum of compound S2.

Figure 10:
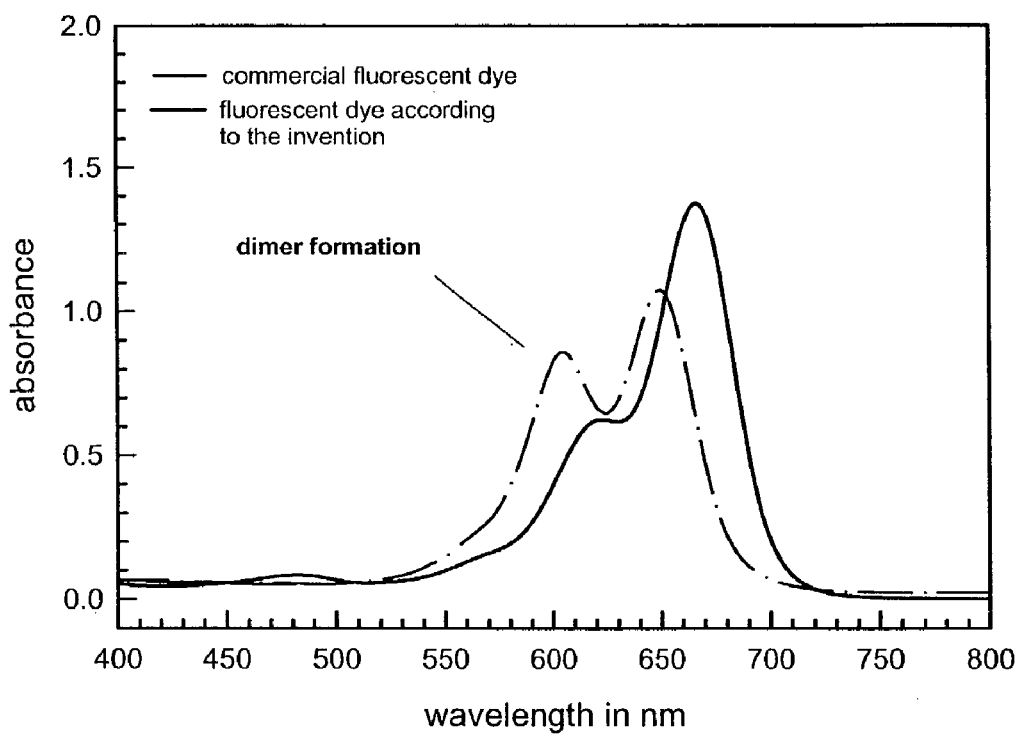

FIG. 10 Absorption- and emission spectrum of the protein conjugate according to example 10.

Figure 11:
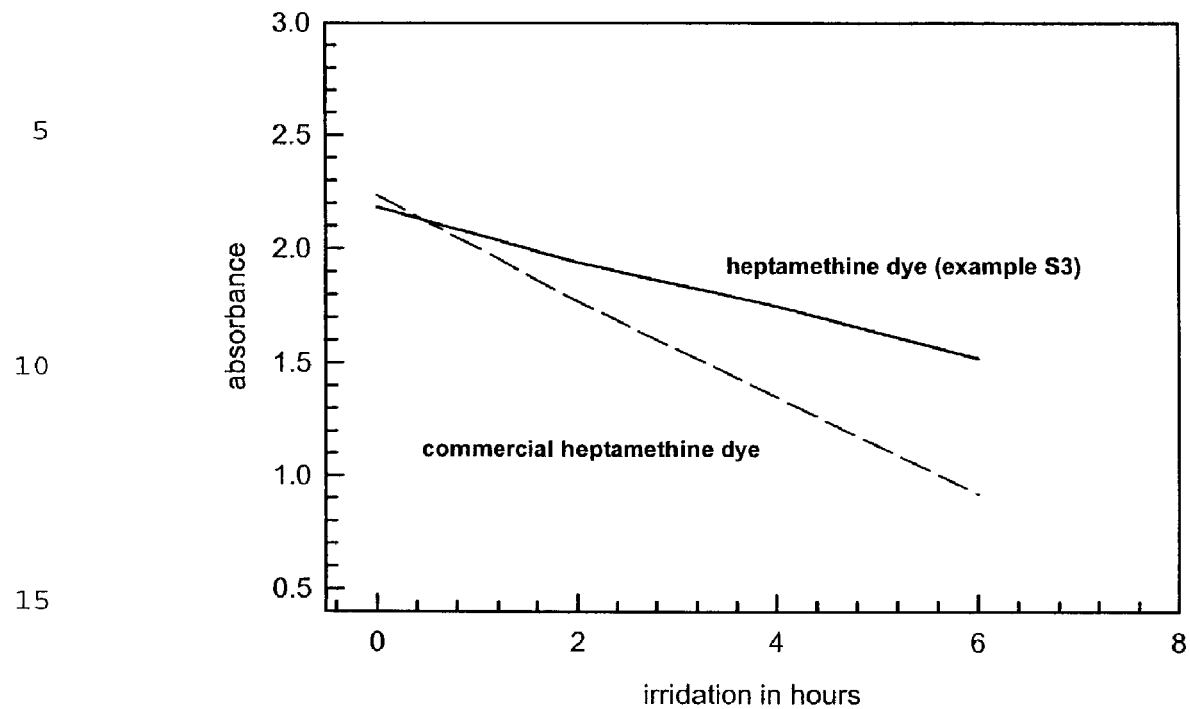

FIG. 11 Photostability of compound S3 (according to example 3).

Figure 12:
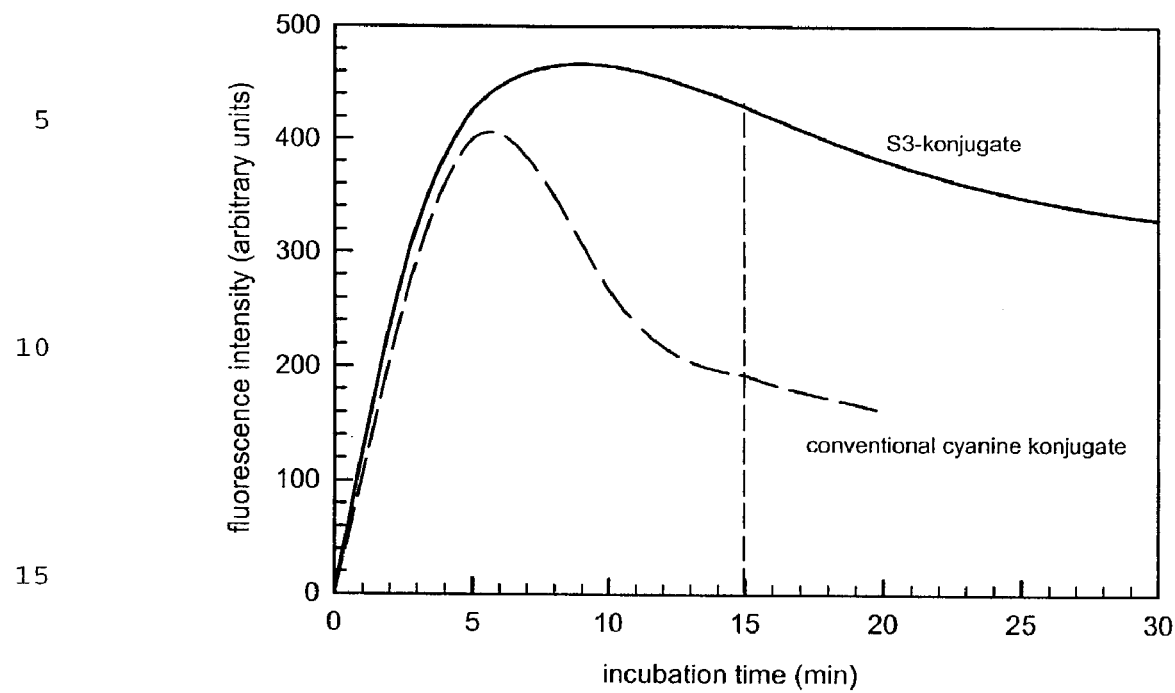

FIG. 12 Fluorescence of the protein conjugate (compound) according to example 10 depending of the incubation time.

Figure 13:
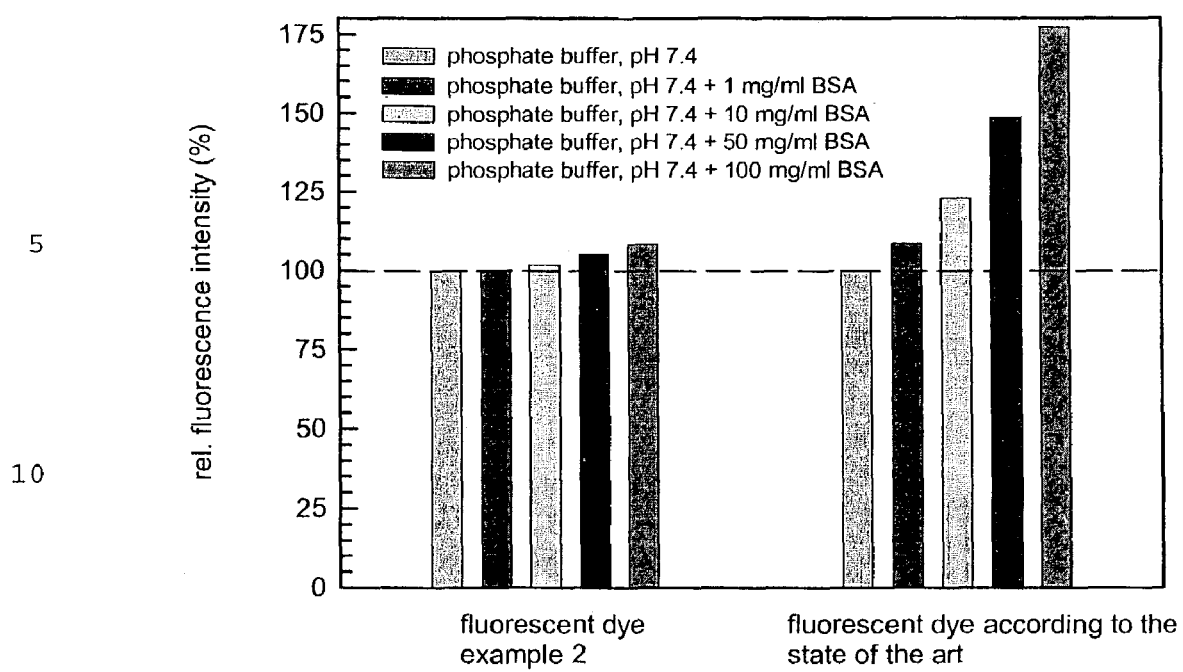

FIG. 13 Fluorescence of compound in the Fluorescence of compound in presence of high protein concentrations presence of high protein concentrations.

PREPARATION OF DYES OF THE SYMMETRICAL 3-SPIRO-1'-CYCLOHEXAN INDOLE TYPE

Example 1

Synthesis of Dye S1

Preparation of 2-methyl-3-spiro-1'-cyclohexan-5-sulfo-3H-indole; Potassium Salt (FIG. 1, 1a)

30 mmol (5.646 g) phenylhydrazine sulfonic acid is heated with 60 mmol (7.572 g) cyclohexylmethylketone and 60 mmol (5.889 g) potassium acetate in 30 ml glacial acetic acid for 6 h under reflux. Subsequently the volatile components were evaporated under reduced pressure. The brown residue is transferred into an extraction thimble and extracted with 200 ml 2-propanole using a Soxleth apparatus. The product starts crystallising in the flask even in the heat, after cooling it is filtered with suction and dried in vacuum.

Yield: 6.044 g (66%)

Preparation of 1-(5-carboxypentyl)-2-methyl-3-spiro-1'-cyclohexan-5-sulfo-3H-indolium bromide; potassium salt (1b)

4.5 mmol (1.418 g) 2-methyl-3-spiro-1'-cyclohexan-5-sulfo-3H-indole is mixed with 5.5 mmol (1.073 g) 6-bromo-hexanoic acid and reacted in the melt at 110° C. for 2.5 h. After cooling the mixture is triturated with acetone, filtered, repeatedly washed with acetone and finally dried in vacuum.

Yield: 1.505 g (66%)

The quaternary spiro-indole (2c) is the key component for the further steps in the synthesis.

Dye S1

1-(5-carboxypentyl)-2-[5-(1-(5-carboxypentyl)-1,3-dihydro-3-spiro-1'-cyclohexan-5-sulfo-2H-indole-2-yliden)-propenyl]-3-spiro-1'-cyclohexan-5-sulfo-3H-indolium hydroxide, inner salt, potassium salt: (FIG. 2, 1c)

0.4 mmol (205 mg) 1-(5-carboxypentyl)-2-methyl-3-spiro-1'-cyclohexan-5-sulfo-3H-indolium bromide (potassium salt) together with 1 mmol (148 mg) triethoxymethane in 2 ml pyridine are heated under reflux for 30 minutes. After cooling the crude dye is precipitated with ether and purified by preparative HPLC using RP-18 and ethanol:water gradient.

According to this procedure cyanine dyes with longer polymethine chain are also accessible.

Example 2

Synthesis of Dye S2

1-(5-carboxypentyl)-2-[5-(1-(5-carboxypentyl)-1,3-dihydro-3-spiro-1'-cyclohexan-5-sulfo-2H-indole-2-yliden)-penta-1,3-dienyl]-3-spiro-1'-cyclohexan-5-sulfo-3H-indolium hydroxide, inner salt, potassium salt: (FIG. 2, 1d)

0.22 mmol (111.6 mg) 1-(5-carboxypentyl)-2-methyl-3-spiro-1'-cyclohexan-5-sulfoindolium bromide (potassium salt) were dissolved in 1 ml of dry pyridine and refluxed. Then 0.5 ml tetraethoxypropane is added in portions over a period of 2.5 h. The precipitated dye is repeatedly washed with pyridine, finally washed with diethylether and purified by preparative HPLC using methanol water gradient on silicagel RP-18.

Example 3

Synthesis of Dye S3

1-(5-carboxypentyl)-2-[5-(1-(5-carboxypentyl)-1,3-dihydro-3-spiro-1'-cyclohexan-5-sulfo-2H-indole-2-yliden)-hepta-1,3,5-trienyl]-3-spiro-1'-cyclohexan-5-sulfo-3H-indolium hydroxide, inner salt, potassium salt (FIG. 2, 1*e*)

0.32 mmol (125 mg) 1-(5-carboxypentyl)-2-methyl-3-spiro-1'-cyclohexan-5-sulfoindolium bromide (potassium salt) together with 0.16 mmol (45 mg) glutaconedianil hydrochloride and 0.65 mmol (63 mg) potassium acetate in a mixture of 2 ml acetic anhydride and 0.5 ml glacial acetic acid are heated to reflux for 30 minutes. The crude dye is precipitated with acetone, filtered off and purified by preparative HPLC using a ethanol-water gradient on silicagel RP-18.

Preparation of Dyes of the Asymmetric 3-spiro-1'-cyclohexan indole type

Example 4

Synthesis of Dye S4

2-methyl-3-spiro-1'-cyclohexan-3H-indole (FIG. 3, 2*a*)

1.25 mol (135.2 g) phenylhydrazine and 1.5 mol (189.3 g) cyclohexylmethylketone in 1.25 l glacial acetic acid are heated to reflux for 3 h. The glacial acetic acid is evaporated in vacuum, 1 l of water is added to the residue and the solution is extracted 4× with ether. After the etheric layer is washed with sodium hyrogencarbonate solution and dried with sodium sulfate, the ether is evaporated and the residue is distilled in vacuum.
bp. (2 mbar): 133-136° C.
yield: 192.6 g (77%)

1-(4-sulfobutyl)-2-methyl-3-spiro-1'cyclohexan-3H-indolium hydroxide Inner Salt (FIG. 3, 2*b*)

28.7 mmol (5.72 g) 2-methyl-3-spiro-1'-cyclohexan-3H-indole and 32 mmol (4.36 g) butanesultone are heated to 120° C. for 4 h. After cooling the mixture is triturated with 50 ml ether, washed 2× with ethylacetate, again with ether and finally dried in vacuum.
Yield: 7.93 g (82%)

2-(4-acetanilino-1,3-butadienyl)-3-spiro-1'-cyclohexan-1-(4-sulfobutyl)-3H-indolium hydroxide inner salt (FIG. 3, 2*c*)

4*mmol* (1.34 g) 1-(4-sulfobutyl)-2-methyl-3-spiro-1'cyclohexan-3H-indolium hydroxide inner salt and 5 mmol malondianil (prepared from 5 mmol (1.62 g) malondianilhydroperchlorate and 5 mmol (490 mg) potassiumacetate in abs. ethanol, diluted with diethylether and evaporation of the filtrate) in 5 ml acetic anhydride and 5 ml glacial acetic acid are heated at 80° C. for 3 h. The solvent is evaporated in vacuum and the residue triturated with ether, filtered off and washed with ether until the filtrate is colourless. The product is dried in vacuum and used for the next steps without further purification.
Yield: 2.00 g (98% d.Th.)

1-(4-acetoxybutyl)-2-methyl-3-spiro-1'-cyclohexan-3H-indolium iodide (FIG. 3, 2*d*)

0.27 mol (49.8 g) 2-methyl-3-spiro-1'-cyclohexan-3H-indole and 0.27 mol (70.0 g) 4-iodobutylacetate are heated for 5 h at 110° C. After cooling the residue is dissolved in small amount of methylenehloride and stirred with 500 ml of ether. After stirring for a while the product crystallises, it is sucked of, washed with ether and dried in vacuum.
Yield: 104.9 g (87%)

Analogous to the preparation of 1-(4-acetoxybutyl)-2-methyl-3-spiro-1'-cyclohexan-3H-indolium iodide (2*d*) the according derivatives of 2-methylbenzoxazole, 2-methylbenzothiazole, 4-methylpyridine and 4 methylchinoline are accessible.

1-(4-acetoxybutyl)-2-methyl benzoxazolium iodide (2*e*)

10 mmol (1.33 g) 2-methylbenzoxazole and 10 mmol (2.42 g) 4-iodobutylacetate are heated for 6 h at 130° C. and after cooling mixed with 10 ml of ethylacetate. The crystals obtained are washed with ether and dried in vacuum.
Yield: 2.17 g (58%)

1-(4-acetoxybutyl)-2-methyl benzothiazolium iodide (2*f*)

10 mmol (1.49 g) 2-methyl-benzothiazole and 10 mmol (2.42 g) 4-iodobutylacetate are heated for 4 h at 120° C. and after cooling mixed with ether sucked off, again washed with ether and dried in vacuum.
Yield: 3.01 g (77%)

1-(4-acetoxybutyl)-4-methyl-pyridinium iodide (2*g*)

10 mmol (0.93 g) γ-picoline and 10 mmol (2.42 g) 4-iodobutylacetate are heated 4 h at 120° C. and after cooling repeatedly stirred with ether, decanted a finally dried in vacuum.
Yield: 2.35 g (70% d.Th.) viscous mass 1-(4-acetoxybutyl)-4-methyl-chinolinium iodide (2*h*)

10 mmol (1.43 g) lepidine and 10 mmol (2.42 g) 4-iodobutylacetate are heated 4 h at 120° C. and after cooling repeatedly stirred with ether, decanted a finally dried in vacuum.
Yield: 3.13 g (81% d.Th.) viscous mass

Dye S4

1-(4-hydroxybutyl)-2-[5-(1,3-dihydro-1-(4-sulfobutyl)-3-spiro-1'-cyclohexan-2H-indole-2-ylidene)-penta-1,3-dienyl]-benzoxazolium hydroxide inner salt (FIG. 4, 2*i*)

0.20 mmol (101 mg) 2-(4-acetanilino-1,3-butadienyl)-3-spiro-1'cyclohexan-1-(4-sulfobutyl)-3H-indolium hydroxide inner salt, 0.21 mmol (79 mg) 1-(4-acetoxybutyl)-benzoxazolium iodide and 0.21 mmol (29.3 μl) triethylamine are refluxed in 1 ml abs. ethanol for 30 min. After cooling 5 ml ether is added and decanted. The residue is dissolved in a mixture of 1 ml conc. HCl and 9 ml methanol and left overnight at 4° C. The solvent is evaporated in vacuum and the residue is purified by chromatography on silicagel RP-18 and acetonitrile-water (1:1).

Example 5

Synthesis of Dye S5

1-(4-hydroxybutyl)-2-[5-(1,3-dihydro-1-(4-sulfobutyl)-3-spiro-1'-cyclohexan-2H-indole-2-yliden)-penta-1,3-dienyl]-benzothiazolium hydroxide inner salt (FIG. 4, 2*j*)

Analogously to the procedure cited above 0.21 mmol (82 mg) 1-(4-acetoxybutyl)-benzothiazolium iodide are reacted with the appropriate reagents.

Example 6

Synthesis of Dye S6

1-(4-hydroxybutyl)-4-[5-(1,3-dihydro-1-(4-sulfobutyl)-3-spiro-1'-cyclohexan-2H-indole-2-yliden)-penta-1,3-dienyl]-pyridinium hydroxide inner salt (FIG. 4, 2*k*)

Analogously to the procedure cited above 0.21 mmol (71 mg) 1-(4-acetoxybutyl)-pyridinium iodide are reacted with the appropriate reagents.

Example 7

Synthesis of Dye S7

1-(4-hydroxybutyl)-4-[5-(1,3-dihydro-1-(4-sulfobutyl)-3-spiro-1'-cyclohexan-2H-indole-2-yliden)-penta-1,3-dienyl]-chinolinium hydroxide inner salt (FIG. 4, 2*l*)

Analogously to the procedure cited above 0.21 mmol (81 mg) 1-(4-acetoxybutyl)-chinolinium iodide are reacted with the appropriate reagents.

Due to the state of the art, the hydroxyl substituted fluorophores, prepared according to 2*i*-2*l* may be converted to the corresponding phosphoramidites with 2-cyanoethyl-N,N-diisopropyl-chlorophosphoramidite and coupled with DNA.

Preparation of Dyes of the Asymmetric 3-spiro-1'-4-tetrahydropyrane-indole Type

Example 8

Synthesis of Dye S8

2-methyl-5-sulfo-3-spiro-4'-tetrahydropyrane-3H-indole (FIG. 5, 3*a*)

40 *mmol* (7.53 g) phenylhydrazine-4-sulfonic acid and 44 mmol 4-acetyltetrahydropyrane in 40 ml glacial acetic acid were refluxed 48 h under nitrogen. Afterwards the precipitate is filtered and the acetic acid is evaporated. The residue is dissolved in a small amount of water and 4 ml of 10M NaOH is added. After evaporation to dryness the residue is extracted with 2-propanole. The extract is evaporated and the residue dried in vacuum.

Yield: 6.94 g (57%)

1-ethyl-2-methyl-5-sulfo-3-spiro-4'-tetrahydropyrane-3H-indolium hydroxide inner salt (FIG. 5, 3*b*)

5.2 mmol (1.58 g) 2-methyl-5-sulfo-3-spiro-4'-tetra-hydropyrane-3H-indole and 5.72 mmol (882 mg) diethylsulfate are heated for 5 h at 110° C. in 3 ml 1.2-dichlorobenzene. After cooling the mixture is diluted with acetone and filtered. The resulting cake is thoroughly washed with acetone and dried in vacuum.

Yield: 1.08 g (67%)

1-(5-carboxypentyl)-2-methyl-5-sulfo-3-spiro-4'-tetrahydropyrane-3H-indolium inner salt (FIG. 5, 3*c*)

10 mmol (3.03 g) 2-ethyl-5-sulfo-3-spiro-4'-tetrahydro-yrane-3H-indole and 15 mmol (22.93 g) 6-bromohexanoic acid are heated in 10 ml of 1,2-dichlorobenzene for 24 h at 120° C. After cooling the solution is diluted with acetone and decanted. The precipitate is triturated with hot 2-propanole, cooled, filtered, washed with 2-propanole and acetone and finally dried in vacuum.

Yield 3.07 g (78%)

2-(4-acetanilino-1,3-butadienyl)-1-ethyl-3-spiro-4'-tetrahydropyrane-5-sulfo-3H-indolium hydroxide inner salt (FIG. 5, 3*d*)

3 *mmol* (0.93 g) 1-ethyl-2-methyl-3-spiro-4'-tetrahydropyrane-5-sulfo-3H-indolium toluenesulfonate and 3.6 mmol malondianile (prepared from 3.6 mmol (prepared from 3.6 mmol (1.165 g) malondianilehydroperchlorate and 3.6 mmol (353 mg) potassium acetate in abs. ethanol, diluted with diethylether and evaporation of the filtrate) in 15 ml of a mixture of glacial acetic acid and acetic anhydride (1:1 v/v) and heated for 3 h at 80° C. The solvent is evaporated in vacuum and the residue triturated with ether, filtered off and washed with ether until the filtrate is colourless.

The product is dried in vacuum.

Yield: 1.33 g (92%)

Dye S8

1-(5-carboxypentyl)-2-[5-(1,3-dihydro-1-ethyl)-3-spiro-4'-tetrahydropyrane-5-sulfo-2H-indole-2-yliden)-penta-1,3-dienyl]-3-spiro-4'-tetrahydropyrane-5-sulfo-3H-indolium hydroxide inner salt potassium salt, (FIG. 5, 3*e*)

2.5 mmol (1.20 g) 2-(4-acetanilino-1,3-butadienyl)-3-spiro-4'-tetrahydropyrane-1-ethyl-5-sulfo-3H-indolium hydroxide inner salt in a mixture of 5 ml pyridine and 5 ml acetic anhydride are treated with 2.7 mmol (1.07 g) 1-(5-carboxypentyl)-2-methyl-5-sulfo-3-spiro-4'-tetrahydropyran-3H-indolium inner salt and refluxed for 40 min. The solution is concentrated in vacuum to one third and the crude dye is precipitated with ether and decanted. The residue is dissolved in a small amount of 1M HCl and repreciptated with a saturated solution of KCl. The precipitate is separated, dissolved in water and purified by reversed-phase chromatography on silicagel RP-18 with an acetonitrile-water gradient.

Preparation of dyes of the asymmetric
3-spiro-1'-4'-piperidyl-indole type

Example 9

Syntheses of Dye S9

Synthesis of 2-methyl-3-spiro-4"-(1'-carboxyben-
zyl)-piperidine-3H-indole (FIG. 6, 4*a*)

4.31 g (16.5 mmol) of the piperidylketone and 1.62 g (1.48 ml, 15 mmol) phenylhydrazine are dissolved in 15 ml glacial acetic acid under inert gas atmosphere and refluxed for 3.5 h. The excess acetic acid is distilled in vacuum on a rotary evaporator remaining a brown oil. The oil is taken up in 80 ml of water and extracted thrice with each 40 ml diethylether. The combined organic layers are washed once again with 40 ml of water and dried over magnesiumsulfate. The solvent is distilled off in vacuum on a rotary evaporator. The remaining brown oil is purified by column chromatography (dichloromethane/ethylacetate=2:1) The indole is obtained as reddish oil.

Yield=3.23 g, 9.7 mmol, (64%).

Synthesis of 1-ethyl-2-methyl-3-spiro-4'-(1'-carboxybenzyl)-piperidine-3H-indolenium ethyl sulfate
(FIG. 6, 4*b*)

Under inert gas atmosphere 2.06 g (6 mmol) of 2-methyl-3-spiro-4'-(1'-carboxybenzyl)-piperidine-3H-indole (4*a*) are dissolved in 3 ml toluene. 1.02 g (0.89 ml, 6.6 mmol) diethylsulfate are added through a syringe. The mixture is refluxed for 3.5 h, precipitating a dark purple oil, which turns solid on cooling. The supernatant liquid is decanted and the residue repeatedly washed with small portions of toluene. The solid is purified by columnchromatography with the aid of a gradient system (1. ethylacetate, 2. acetone/glacial acetic acid=10:2). The quaternary indole is eluted twice with the solvent and the product is obtained as highly viscous oil (0.93 g, 1.9 mmol, 32%).

Synthesis of 2-(4-acetanilino-1,3-butadienyl)-1-
ethyl-3-spiro-4'-(1'-carboxybenzyl)-piperidine-3H-indolenium ethyl sulfate (FIG. 6, 4*c*)

0.93 g (1.9 mmol) of the quaternary indole (4*b*) and 2.4 mmol malondianil (prepared from 0.79 g (2.4 mmol) malondianil-hydroperchlorate and 0.23 g (2.4 mmol) potassium acetate in abs. ethanol, diluted with diethylether and evaporation of the filtrate) in 3 ml of acetic anhydride and 3 ml glacial acetic acid are heated for 3 h at 80° C. The solvent is removed under reduced pressure on a rotary evaporator. The solid residue is triturated with diethylether, filtered and washed with ether until the filtrate is colourless. The crude product (1.19 g, 1.8 mmol, 97%) is dried in vacuum and used in the next step without further purification.

Synthesis of 1-carboxypentyl-2-methyl-3-spiro-4'-
(1'-carboxybenzyl)-piperidine-3H-indolium bromide
(FIG. 6, 4*d*)

2.06 g (6 mmol) 2-methyl-3-spiro-4'-(1'-carboxy-benzyl)-piperidine-3H-indole (4*a*) are heated in 5 ml 6-bromohexanoicacid 3.5 h a 120° C. The supernatant is decanted from the reddish solid. Purification is carried out by column chromatography (water/acetic acid=10:2). The quaternary indole is obtained as reddish highly viscous oil (0.95 g, 1.8 mmol, 30%).

Dye S 9

Synthesis of 1-(5-carboxypentyl)-2-[5-(1,3-dihydro-
1-(1-ethyl)-3-spiro-4'-(1'-carboxybenzyl)-piperidine-
2H-indole-2-yliden)-penta-1,3-dienyl]-3-spiro-4'-(1'-
carboxybenzyl)-piperidin-3H-indolenium ethyl
sulfate (FIG. 6, 4*e*)

0.62 g (1.8 mmol) of the hemicyanine (4*c*) and 0.71 g (1.8 mmol) the indole (4*d*) in 3 ml acetic anhydride and 3 ml pyridine are refluxed for 30 min. The mixture is evaporated to dryness in vacuum on a rotary evaporator. The solid residue is taken up in a mixture of 10 ml conc. HCl and 100 ml methanol and left overnight at 4° C. The solvent is distilled off at reduced pressure and the residue is purified by column chromatography (isopropanol:water, 2:1 (v/v)). The dye S9 is obtained as dark blue crystalline solid (0.36 g, 0.38 mmol, 21%).

Synthesis of 1-(5-carboxypentyl)-2-[5-(1,3-dihydro-
1-(1-ethyl)-3-spiro-4'-piperidine-2H-indole-2-
ylidene)-penta-1,3-dienyl]-3-spiro-4'-piperidine-3H-
indolenium ethylsulfate (FIG. 7, 4*f*)

0.36 g (0.38 mmol) of the dye (4*e*) is dissolved under an inertgas atmosphere in 5 ml of chloroform. With a syringe 0.09 g (0.07 ml, 0.46 mmol) of iodotrimethylsilane is added and the mixture is stirred at room temperature until the educt is not detectable again by thinlayer chromatography (isopropanol/water=10:2, v/v). After that 2 ml of methanol is added and the mixture is stirred for 5 min. at room temperature. The liquid components are distilled off in vacuum on a rotary evaporator and the solid residue is purified by column chromatography with the eluent isopropanol:water=2:1. Yield: 0.23 g, 0.3 mmol (80%).

The deprotected dye S9 (4*f*) can be converted into a polyethylen glycole-substituted dye (4*g*) by melting together with glycidyl-PEG.

Absorption spectra of the dyes (S1-S3) prepared in examples 1-3 are shown in FIG. 8.

In order to covalently label target molecules the carbonyl moiety has to be converted into an activated ester (reactive group $R_x$). Due to state of the art, this can be carried out with N-hydroxysuccinimide in the presence of 1-ethyl-3-(3-dimethylaminopropyl) carbodiimide (EDC) in aqueous solution or with dicyclohexylcarbodiimide (DCC) in organic solution (FIG. 2, 1*f*)

Example 10

Coupling of the NHS Activated pentamethine-spiro-cyanine (Compound S2) to Protein 0.2 mg activated dye are added while shaking to 1 mg of bovine serum albumin in 1 ml 10 mM phosphate buffer, pH 8.0. After a reaction time of 60 min, the coupling is stopped by the addition of 40 µl glycine solution (10% m/v, in PBS-buffer, pH 7.4) and the excess of dye is removed through dialysis or gelfiltration.

FIG. 9 shows the emission spectrum of the dye-conjugate obtained with dye S2 (example 2) as described in example 10.

In comparison, FIG. 10 shows the corresponding spectrum of a common conjugate created under identical conditions. A band in the absorption spectrum at about λ=600 nm due to dimer formation which leads to reduced fluorescence can clearly be seen.

The mobility of the fluorescent dye is reduced due to the influence of the bulky spiro-substituent, which leads to an increased photostability. FIG. 11 displays the photostability of the compound S3 prepared according to example 3, determined in 10 mM phosphate buffer, pH 7.4, compared to a commercial state-of-the-art heptamethine dye. Irradiation was performed using a krypton-lamp and 20 mW/cm$^2$ at λ>400 nm.

By determination of the fluorescence of the S3-conjugate, according to example 10, in comparison to a conjugate, created using a common cyanine-dye, the results displayed in FIG. 12 are obtained. The resulting fluorescence of the conjugates, created under identical conditions, was determined at different incubation times after separation of the excess of the dye. The longer the incubation time, the higher the label degree fluorophor:protein. The formation of a narrow maximum is observed with the conjugate according to the state of the art, the resulting fluorescence decreases more than 50% at higher labeling degrees due to self-quenching phemonena. In contrast, conjugates with the fluorescent dye according to the invention (examples 2 and 10) show a substantially reduced tendency towards aggregation and thus exhibit higher fluorescence. The fluorescence of the conjugate with the invention based fluorophor (example 10) after an incubation time of 15 minutes is more than double as high as the one of the conjugate with a state-of-the-art fluorophor.

The spiro-substituent also causes a shielding of the central polymethine chain against the influence of the surroundings of the fluorophor. As known, many fluorophores exhibit a shift of their absorption-maximum towards longer wavelengths and a simultaneous increase of fluorescence with an increase of protein concentration. This is caused by the changed environment created by the protein and the reduced mobility of the fluorescent dye. This effect is minimized with the fluorescent dye according to the invention. As shown in FIG. 13 (normalized display), there only is a minimal increase of fluorescence in the presence of high concentrations of bovine serum albumin (BSA). The fluorescence of the commercial fluorophor, in contrast, is highly dependent on the environment. Latter effect is a very strong disadvantage when analyzing substances in blood serum.

In table 2 the characteristic data of selected fluorescent dyes according to the invention are shown.

TABLE 1

| electrophilic group | nucleophilic group | type of chemical bondage formed |
|---|---|---|
| activated ester[1] | amine/aniline | carboxamide |
| acylazide | amine/aniline | carboxamide |
| acylhalide | amine/aniline | carboxamide |
| acylhalogene | alkohole/phenole | ester |
| acylnitrile | alkohole/phenole | ester |
| acylnitrile | amine/aniline | carboxamide |
| aldehyde | amine/aniline | imine |
| aldehyde/ketone | hydrazine | hydrazone |
| aldehyde/ketone | hydroxylamine | oxime |
| alkylhalogene | amine/aniline | alkylamine |
| alkylhalogene | carbonic acids | ester |
| alkylhalogene | thiole | thio ether |
| alkylhalogene | alcohol/phenol | ether |
| alkylsulfonate | thiole | thio ether |
| alkylsulfonate | carbonic acids | ester |
| alkylsulfonate | alcohol/phenol | ester |

TABLE 1-continued

| electrophilic group | nucleophilic group | type of chemical bondage formed |
|---|---|---|
| anhydride | alcohol/phenol | ester |
| anhydride | amine/aniline | carboxamide |
| arylhalogene | thiole | thiophenole |
| arylhalogene | amine | arylamine |
| aziridine | thiole | thioester |
| boronate | glycole | boronatester |
| carbonic acids | amine/aniline | carboxamide |
| carbonic acids | alcohol | ester |
| carbonic acids | hydrazine | hydrazide |
| carbodiimide | carbonic acids | N-acyl-urea |
| diazoalkane | carbonic acids | ester |
| epoxide | thiole | thio ether |
| haloacetamide | thiole | thio ether |
| halotriazine | amine/aniline | aminotriazine |
| halotriazine | alcohol/phenol | triazinether |
| imidoester | amin/aniline | amidine |
| isocyanate | amine/aniline | urea |
| isocyanate | alcohol/phenol | urethane |
| isothiocyanate | amine/aniline | thiourea |
| maleimide | thiole | thio ether |
| phosphoramidite | alcohol | phosphite triester |
| silylhalogene | alcohol | silyl ether |
| sulfonic acid ester | amine/aniline | alkylamine |
| sulfonic acid ester | carbonic acids | ester |
| sulfonic acid ester | thiole | thio ether |
| sulfonic acid ester | alcohol | ether |
| sulfonic acid ester | amine/aniline | sulfonamide |
| sulfonylchloride | alcohol/phenol | sulfonic acid ester |

[1]activated ester with the general structure —CO-W, where in W is a suitable leaving group, e.g., nitro-, fluoro-, chloro-, cyano-, trifluoromethyl-, tosyl- etc.

TABLE 2 charactareistic data of selected fluorescent dyes according to the invention

| Compound | absorption maximum (nm) | emission-maximum (nm) |
|---|---|---|
| S1* | 557 | 572 |
| S2* | 656 | 672 |
| S3* | 756 | 772 |
| S4** | 612 | 638 |
| S5** | 650 | 676 |
| S6** | 603 | 626 |
| S7** | 702 | 728 |
| S8** | 662 | 684 |
| S9** | 660 | 682 |

*determined in phospate buffer, pH 7.4
**determined in ethanol

What is claimed is:

1. A fluorescent dye having a formula (I)

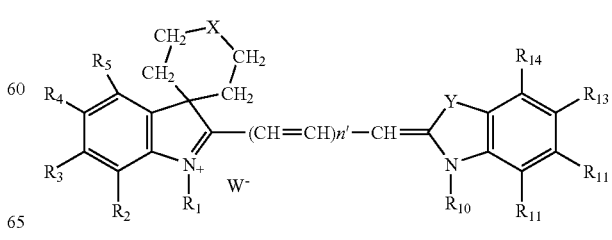

wherein X is

O, or

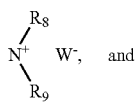

Y is 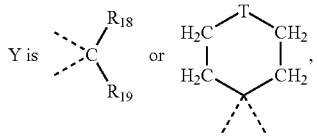

and T is

n' is an integer which is 0, 1, 2, or 3 and

W⁻ is a counter ion, wherein at least one of the substituents $R_1$, $R_{10}$, $R_6$-$R_9$ and $R_{18}$ to $R_{19}$ is a chemical reactive group (Rx) for covalent coupling to a target molecule which is selected from the group consisting of:

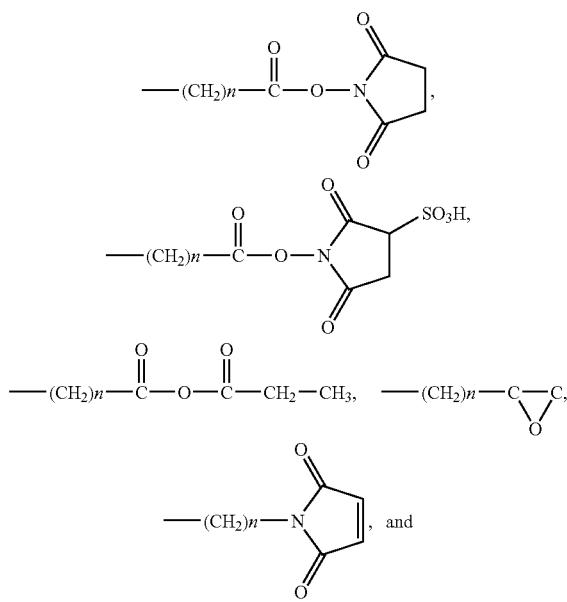

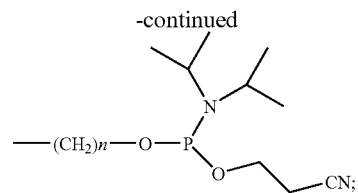

wherein n is 1-8;

and wherein at least one of the substituents $R_1$, $R_4$, $R_{10}$, $R_{13}$, $R_6$ to $R_9$ and $R_{18}$ to $R_{19}$ is a hydrophilic group to promote water solubility selected from the group consisting of sulfonic acids and sulfonates, having a formula

with r equal to 0 to 8 and M⁺ is a metal cation;

and the other substituents $R_1$ to $R_{19}$ are independently selected from the group consisting of H, alkyl ($C_1$-$C_{10}$), alkoxy ($C_1$-$C_{10}$), trifluoromethyl, nitro, and halogen.

2. A fluorescent dye according to claim 1, in which at least one of the substituents $R_1$, $R_{10}$, and $R_8$, $R_9$, is a chemical reactive group (Rx).

3. A fluorescent dye according to claim 1, in which at least one of the substituents $R_1$, $R_4$, $R_8$, $R_9$, $R_{10}$, $R_{13}$, $R_{18}$, $R_{19}$ is a hydrophilic group.

4. A fluorescent dye according to claim 1, in which the counter ion W⁻ is selected from the group consisting of halogenide, tosylate and perchlorate.

5. A fluorescent dye according to claim 1, having a formula:

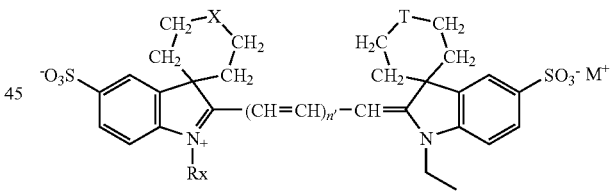

where M⁺ is a metal cation, X, T, Rx and n' are defined according to claim 1.

6. A fluorescent dye according to claim 1, having a formula:

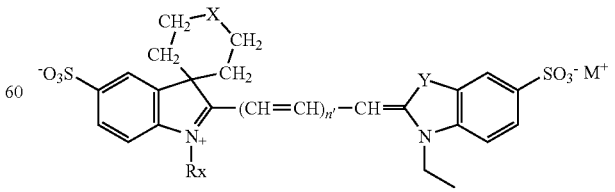

where M⁺ is a metal cation, X, Y, Rx and n' are defined according to claim 1.

7. A fluorescent dye according to claim 1, having a formula:

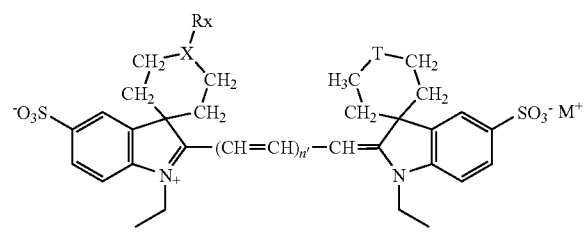

where M⁺ is a metal cation, T, Rx and n' are defined according to claim 1.

8. A fluorescent dye according to claim 1, having a formula:

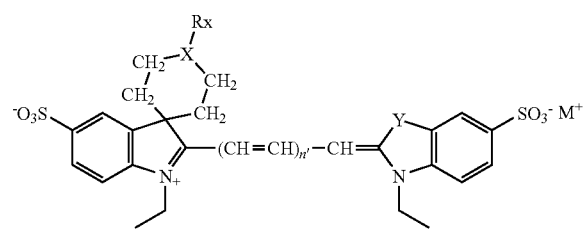

where M⁺ is a metal cation, Y, Rx and n' are defined according to claim 1.

9. A fluorescent dye according to claim 1, having a formula:

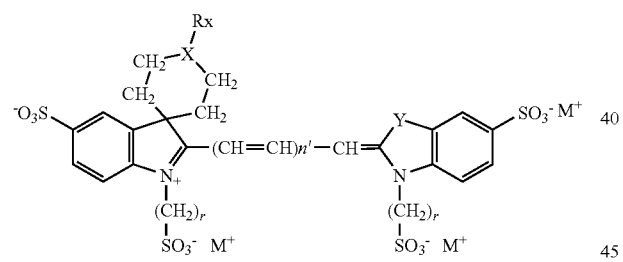

where M⁺ is a metal cation, Rx, Y, r and n' are defined according to claim 1.

10. A fluorescent dye according to claim 1, having a formula:

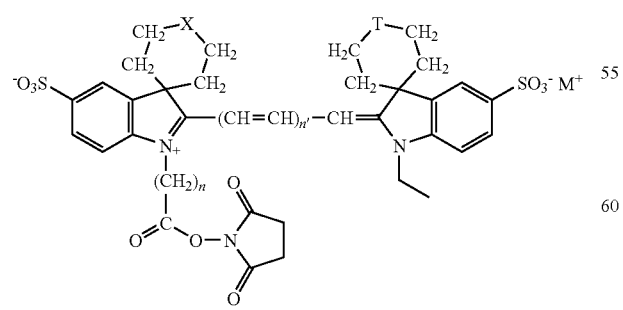

where M⁺ is a metal cation; X, T, n and n' are defined according to claim 1.

11. A fluorescent dye according to claim 1, having a formula:

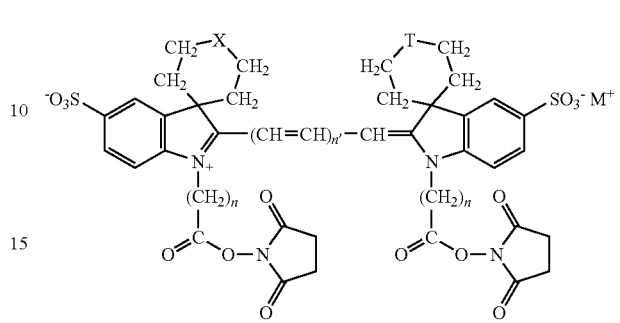

where M⁺ is a metal cation, X, T, n and n' are defined according to claim 1.

12. A fluorescent dye according to claim 1, having a formula:

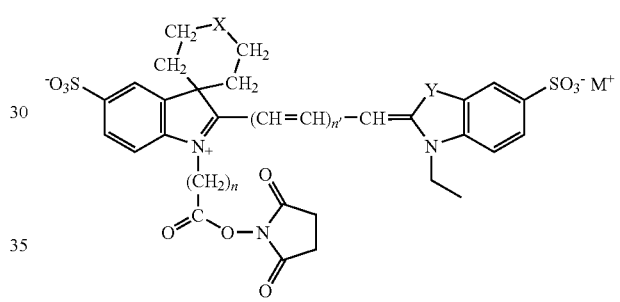

where M⁺ is a metal cation, X, Y, n and n' are defined according to claim 1.

13. A fluorescent dye according to claim 1, having a formula:

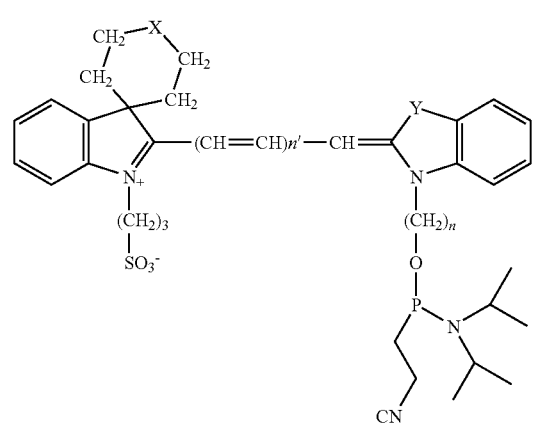

where X, Y, n and n' are defined according to claim 1.

* * * * *